(12) United States Patent
Sogard et al.

(10) Patent No.: US 7,799,038 B2
(45) Date of Patent: Sep. 21, 2010

(54) TRANSLUMENAL APPARATUS, SYSTEM, AND METHOD

(75) Inventors: David J. Sogard, Edina, MN (US); Kent D. Harrison, Maple Grove, MN (US); Leonard B. Richardson, Minneapolis, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 386 days.

(21) Appl. No.: 11/337,162

(22) Filed: Jan. 20, 2006

(65) Prior Publication Data

US 2007/0173930 A1 Jul. 26, 2007

(51) Int. Cl.
*A61B 17/10* (2006.01)

(52) U.S. Cl. ........................ 606/139
(58) Field of Classification Search ........... 606/139, 606/144, 148, 113; 623/2.11, 2.37; 604/264, 604/523, 525; 600/104
See application file for complete search history.

(56) References Cited

U.S. PATENT DOCUMENTS

| 3,671,979 A | 6/1972 | Moulopoulos ............... 3/1 |
| 4,291,420 A | 9/1981 | Reul ........................ 3/1.5 |
| 4,787,901 A | 11/1988 | Baykut ..................... 623/2 |
| 4,809,695 A | 3/1989 | Gwathmey et al. |
| 4,872,874 A | 10/1989 | Taheri ..................... 623/1 |
| 4,935,030 A | 6/1990 | Alonso ..................... 623/2 |
| 4,994,077 A | 2/1991 | Dobben .................... 623/2 |
| 5,002,567 A | 3/1991 | Bona et al. ................ 623/2 |
| 5,141,491 A | 8/1992 | Bowald .................... 604/22 |
| 5,163,953 A | 11/1992 | Vince ...................... 623/2 |
| 5,219,355 A | 6/1993 | Parodi et al. ............. 606/191 |
| 5,254,127 A | 10/1993 | Wholey et al. ........... 606/153 |
| 5,318,525 A | 6/1994 | West et al. |
| 5,327,774 A | 7/1994 | Nguyen et al. ............. 73/37 |
| 5,332,402 A | 7/1994 | Teitelbaum ................ 623/2 |
| 5,370,685 A | 12/1994 | Stevens .................... 623/2 |
| 5,411,552 A | 5/1995 | Andersen et al. ........... 623/2 |
| 5,469,868 A | 11/1995 | Reger ..................... 128/898 |
| 5,480,423 A | 1/1996 | Ravenscroft et al. ......... 623/1 |
| 5,500,014 A | 3/1996 | Quijano et al. ............. 623/2 |
| 5,545,214 A | 8/1996 | Stevens .................... 623/2 |
| 5,554,185 A | 9/1996 | Block et al. ............... 623/2 |
| 5,643,208 A | 7/1997 | Parodi ..................... 604/96 |
| 5,693,087 A | 12/1997 | Parodi ..................... 623/1 |
| 5,713,953 A | 2/1998 | Vallana et al. ............. 623/2 |
| 5,716,367 A * | 2/1998 | Koike et al. .............. 606/144 |

(Continued)

FOREIGN PATENT DOCUMENTS

EP 0 380 666 8/1990

(Continued)

OTHER PUBLICATIONS

International Search Report (7 pgs.).

*Primary Examiner*—(Jackie) Tan-Uyen T Ho
*Assistant Examiner*—Dianne Dornbusch
(74) *Attorney, Agent, or Firm*—Brooks, Cameron & Huebsch, PLLC

(57) ABSTRACT

Methods, apparatus, and systems for altering the configuration of a heart valve. Methods, apparatus, and systems include the use of a cord delivered into the heart by a delivery catheter that can be manipulated by a receiving catheter so as to improve the heart valve function.

7 Claims, 15 Drawing Sheets

U.S. PATENT DOCUMENTS

| | | | |
|---|---|---|---|
| 5,716,370 A | 2/1998 | Williamson, IV et al. | 606/153 |
| 5,735,859 A | 4/1998 | Fischell et al. | 606/108 |
| 5,741,277 A * | 4/1998 | Gordon et al. | 606/144 |
| 5,741,326 A | 4/1998 | Solovay | 623/1 |
| 5,741,333 A | 4/1998 | Frid | 623/12 |
| 5,800,506 A | 9/1998 | Perouse | 623/1 |
| 5,824,061 A | 10/1998 | Quijano et al. | 623/2 |
| 5,879,320 A | 3/1999 | Cazenave | 604/8 |
| 5,895,419 A | 4/1999 | Tweden et al. | 623/2 |
| 5,910,170 A | 6/1999 | Reimink et al. | 623/2 |
| 5,954,732 A * | 9/1999 | Hart et al. | 606/144 |
| 6,010,531 A | 1/2000 | Donlon et al. | 623/2 |
| 6,042,607 A | 3/2000 | Williamson, IV et al. | 623/2 |
| 6,139,575 A | 10/2000 | Shu et al. | 623/2.12 |
| 6,165,183 A * | 12/2000 | Kuehn et al. | 606/139 |
| 6,190,401 B1 | 2/2001 | Green et al. | |
| 6,258,069 B1 | 7/2001 | Carpentier et al. | 604/208 |
| 6,287,334 B1 | 9/2001 | Moll et al. | 623/1.24 |
| 6,312,447 B1 | 11/2001 | Grimes | 606/219 |
| 6,332,893 B1 | 12/2001 | Mortier et al. | |
| 6,355,030 B1 | 3/2002 | Aldrich et al. | 606/28 |
| 6,402,780 B2 | 6/2002 | Williamson, IV et al. | 623/2.11 |
| 6,419,696 B1 | 7/2002 | Ortiz et al. | 623/2.37 |
| 6,425,916 B1 | 7/2002 | Garrison et al. | 623/2.11 |
| 6,440,164 B1 | 8/2002 | DiMatteo et al. | 623/1.24 |
| 6,451,054 B1 | 9/2002 | Stevens | 623/2.11 |
| 6,454,799 B1 | 9/2002 | Schreck | 623/2.18 |
| 6,461,366 B1 | 10/2002 | Seguin | 606/144 |
| 6,503,272 B2 | 1/2003 | Duerig et al. | 623/1.24 |
| 6,508,833 B2 | 1/2003 | Pavcnik et al. | 623/1.15 |
| 6,564,805 B2 | 5/2003 | Garrison et al. | 128/898 |
| 6,569,196 B1 | 5/2003 | Vesely | 623/2.14 |
| 6,602,286 B1 | 8/2003 | Strecker | 623/1.24 |
| 6,626,930 B1 * | 9/2003 | Allen et al. | 606/213 |
| 6,629,534 B1 | 10/2003 | St. Goar et al. | 128/898 |
| 6,635,085 B1 | 10/2003 | Caffey et al. | 623/2.1 |
| 6,666,885 B2 | 12/2003 | Moe | 623/2.12 |
| 6,666,886 B1 | 12/2003 | Tranquillo et al. | 623/2.42 |
| 6,669,725 B2 | 12/2003 | Scott | 623/2.36 |
| 6,673,109 B2 | 1/2004 | Cox | 623/2.12 |
| 6,676,698 B2 | 1/2004 | McGuckin, Jr. et al. | 623/1.24 |
| 6,676,702 B2 | 1/2004 | Mathis | 623/2.36 |
| 6,682,558 B2 | 1/2004 | Tu et al. | 623/2.11 |
| 6,682,559 B2 | 1/2004 | Myers et al. | 623/2.13 |
| 6,685,739 B2 | 2/2004 | DiMatteo et al. | 623/1.24 |
| 6,692,512 B2 | 2/2004 | Jang | 606/200 |
| 6,695,866 B1 | 2/2004 | Kuehn et al. | 606/213 |
| 6,695,878 B2 | 2/2004 | McGuckin, Jr. et al. | 623/1.19 |
| 6,702,826 B2 | 3/2004 | Liddicoat et al. | 606/151 |
| 6,709,456 B2 | 3/2004 | Langberg et al. | 623/2.37 |
| 6,709,457 B1 | 3/2004 | Otte et al. | 623/2.4 |
| 6,716,241 B2 | 4/2004 | Wilder et al. | 623/1.24 |
| 6,716,244 B2 | 4/2004 | Klaco | 623/2.4 |
| 6,719,767 B1 | 4/2004 | Kimblad | 606/151 |
| 6,719,784 B2 | 4/2004 | Henderson | 623/1.44 |
| 6,719,786 B2 | 4/2004 | Ryan et al. | 623/2.11 |
| 6,719,787 B2 | 4/2004 | Cox | 623/2.12 |
| 6,719,788 B2 | 4/2004 | Cox | 623/2.12 |
| 6,719,789 B2 | 4/2004 | Cox | 623/2.13 |
| 6,719,790 B2 | 4/2004 | Brendzel et al. | 623/2.4 |
| 6,723,038 B1 | 4/2004 | Schroeder et al. | 600/16 |
| 6,723,122 B2 | 4/2004 | Yang et al. | 623/2.1 |
| 6,723,123 B1 | 4/2004 | Kazatchkov et al. | 623/2.2 |
| 6,726,715 B2 | 4/2004 | Sutherland | 623/2.1 |
| 6,726,716 B2 | 4/2004 | Marquez | 623/2.36 |
| 6,726,717 B2 | 4/2004 | Alfieri et al. | 623/2.36 |
| 6,730,118 B2 | 5/2004 | Spenser et al. | 623/1.24 |
| 6,730,121 B2 | 5/2004 | Ortiz et al. | 623/2.17 |
| 6,730,122 B1 | 5/2004 | Pan et al. | 623/2.33 |
| 6,736,845 B2 | 5/2004 | Marquez et al. | 623/2.11 |
| 6,736,846 B2 | 5/2004 | Cox | 623/2.12 |
| 6,749,630 B2 | 6/2004 | McCarthy et al. | 623/2.36 |
| 6,752,813 B2 | 6/2004 | Goldfarb et al. | 606/139 |
| 6,752,828 B2 | 6/2004 | Thornton | 623/1.24 |
| 6,755,857 B2 | 6/2004 | Peterson et al. | 623/2.17 |
| 6,761,734 B2 | 7/2004 | Suhr | 623/1.35 |
| 6,761,735 B2 | 7/2004 | Eberhardt et al. | 623/2.1 |
| 6,764,494 B2 | 7/2004 | Menz et al. | 606/159 |
| 6,764,508 B1 | 7/2004 | Roehe et al. | 623/2.11 |
| 6,764,509 B2 | 7/2004 | Chinn et al. | 623/2.12 |
| 6,764,510 B2 | 7/2004 | Vidlund et al. | 623/2.34 |
| 6,767,362 B2 | 7/2004 | Schreck | 623/2.11 |
| 6,769,434 B2 | 8/2004 | Liddicoat et al. | 128/898 |
| 6,770,083 B2 | 8/2004 | Seguin | 606/142 |
| 6,780,200 B2 | 8/2004 | Jansen | 623/2.17 |
| 6,786,924 B2 | 9/2004 | Ryan et al. | 623/2.36 |
| 6,786,925 B1 | 9/2004 | Schoon et al. | 623/2.38 |
| 6,790,229 B1 | 9/2004 | Berreklouw | 623/2.1 |
| 6,790,230 B2 | 9/2004 | Beyersdorf et al. | 623/2.18 |
| 6,790,231 B2 | 9/2004 | Liddicoat et al. | 623/2.37 |
| 6,793,673 B2 | 9/2004 | Kowalsky et al. | 623/2.36 |
| 6,797,000 B2 | 9/2004 | Simpson et al. | 623/2.15 |
| 6,797,001 B2 | 9/2004 | Mathis et al. | 623/2.37 |
| 6,797,002 B2 | 9/2004 | Spence et al. | 623/2.38 |
| 6,802,860 B2 | 10/2004 | Cosgrove et al. | 623/2.11 |
| 6,805,710 B2 | 10/2004 | Bolling et al. | 623/2.36 |
| 6,805,711 B2 | 10/2004 | Quijano et al. | 623/2.37 |
| 6,810,882 B2 | 11/2004 | Langberg et al. | 128/898 |
| 6,821,297 B2 | 11/2004 | Snyders | 623/2.18 |
| 6,824,562 B2 | 11/2004 | Mathis et al. | 623/2.36 |
| 6,830,584 B1 | 12/2004 | Seguin | 623/2.11 |
| 6,830,585 B1 | 12/2004 | Artof et al. | 623/2.11 |
| 6,837,902 B2 | 1/2005 | Nguyen et al. | 623/2.13 |
| 6,840,246 B2 | 1/2005 | Downing | 128/898 |
| 6,840,957 B2 | 1/2005 | DiMatteo et al. | 623/1.24 |
| 6,846,324 B2 | 1/2005 | Stobie | 623/2.11 |
| 6,846,325 B2 | 1/2005 | Liddicoat | 623/2.4 |
| 6,858,039 B2 | 2/2005 | McCarthy | 623/2.36 |
| 6,869,444 B2 | 3/2005 | Gabbay | 623/2.36 |
| 6,872,226 B2 | 3/2005 | Cali et al. | 623/2.13 |
| 6,875,224 B2 | 4/2005 | Grimes | 606/219 |
| 6,875,230 B1 | 4/2005 | Morita et al. | 623/2.12 |
| 6,875,231 B2 | 4/2005 | Anduiza et al. | 623/2.14 |
| 6,881,199 B2 | 4/2005 | Wilk et al. | 604/9 |
| 6,881,224 B2 | 4/2005 | Kruse et al. | 623/2.11 |
| 6,883,522 B2 | 4/2005 | Spence et al. | 128/898 |
| 6,890,352 B1 | 5/2005 | Lentell | 623/2.27 |
| 6,890,353 B2 | 5/2005 | Cohn et al. | 623/2.37 |
| 6,893,459 B1 | 5/2005 | Macoviak | 623/2.11 |
| 6,893,460 B2 | 5/2005 | Spenser et al. | 623/2.14 |
| 6,896,700 B2 | 5/2005 | Lu et al. | 623/2.34 |
| 6,902,576 B2 | 6/2005 | Drasler et al. | 623/1.24 |
| 6,908,478 B2 | 6/2005 | Alferness et al. | 623/1.11 |
| 6,908,481 B2 | 6/2005 | Cribier | 623/2.11 |
| 6,911,043 B2 | 6/2005 | Myers et al. | 623/2.13 |
| 6,913,608 B2 | 7/2005 | Liddicoat et al. | 606/151 |
| 6,916,338 B2 | 7/2005 | Speziali | 623/2.12 |
| 6,918,917 B1 | 7/2005 | Nguyen et al. | 606/139 |
| 6,921,407 B2 | 7/2005 | Nguyen et al. | 606/142 |
| 6,921,811 B2 | 7/2005 | Zamora et al. | 536/21 |
| 6,926,715 B1 | 8/2005 | Hauck et al. | 606/41 |
| 6,926,730 B1 | 8/2005 | Nguyen et al. | 606/213 |
| 6,929,653 B2 | 8/2005 | Strecter | 606/200 |
| 6,932,838 B2 | 8/2005 | Schwartz et al. | 623/1.23 |
| 6,936,067 B2 | 8/2005 | Buchanan | 623/2.28 |
| 6,939,359 B2 | 9/2005 | Tu et al. | 606/159 |
| 6,942,694 B2 | 9/2005 | Liddicoat et al. | 623/2.36 |
| 6,945,957 B2 | 9/2005 | Freyman | 604/96.01 |
| 6,945,978 B1 | 9/2005 | Hyde | 606/142 |
| 6,945,996 B2 | 9/2005 | Sedransk | 623/2.12 |
| 6,945,997 B2 | 9/2005 | Huynh et al. | 623/2.17 |
| 6,949,122 B2 | 9/2005 | Adams et al. | 623/2.36 |
| 6,951,571 B1 | 10/2005 | Srivastava | 623/1.24 |
| 6,951,573 B1 | 10/2005 | Dilling | 623/2.2 |

| Patent/Pub No. | Date | Inventor | Class |
|---|---|---|---|
| 6,953,332 B1 | 10/2005 | Kurk et al. | 425/275 |
| 6,955,689 B2 | 10/2005 | Ryan et al. | 623/2.36 |
| 6,958,076 B2 | 10/2005 | Acosta et al. | 623/1.24 |
| 6,962,605 B2 | 11/2005 | Cosgrove et al. | 623/2.36 |
| 6,964,682 B2 | 11/2005 | Nguyen-Thien-Nhon et al. | 623/2.11 |
| 6,964,683 B2 | 11/2005 | Kowalsky et al. | 623/2.36 |
| 6,964,684 B2 | 11/2005 | Ortiz et al. | 623/2.37 |
| 6,966,925 B2 | 11/2005 | Stobie | 623/2.11 |
| 6,966,926 B2 | 11/2005 | Mathis | 623/2.36 |
| 6,974,464 B2 | 12/2005 | Quijano et al. | 606/108 |
| 6,974,474 B2 | 12/2005 | Pavcnik et al. | 623/1.24 |
| 6,974,476 B2 | 12/2005 | McGuckin, Jr. et al. | 623/2.36 |
| 6,976,995 B2 | 12/2005 | Mathis et al. | 623/2.37 |
| 6,979,350 B2 | 12/2005 | Moll et al. | 623/1.24 |
| 6,986,775 B2 | 1/2006 | Morales et al. | |
| 6,989,027 B2 | 1/2006 | Allen et al. | 623/2.18 |
| 6,989,028 B2 | 1/2006 | Lashinski et al. | 623/2.37 |
| 6,997,950 B2 | 2/2006 | Chawla | 623/2.1 |
| 6,997,951 B2 | 2/2006 | Solem et al. | 623/2.37 |
| 7,004,176 B2 | 2/2006 | Lau | 128/898 |
| 7,007,396 B2 | 3/2006 | Rudko et al. | 33/512 |
| 7,011,669 B2 | 3/2006 | Kimblad | 606/151 |
| 7,011,681 B2 | 3/2006 | Vesely | 623/2.11 |
| 7,011,682 B2 | 3/2006 | Lahsinski et al. | 623/2.37 |
| 7,018,406 B2 | 3/2006 | Seguin et al. | 623/2.1 |
| 7,018,407 B1 | 3/2006 | Wright et al. | 623/2.11 |
| 7,018,408 B2 | 3/2006 | Bailey et al. | 623/2.11 |
| 7,022,134 B1 | 4/2006 | Quijano et al. | 623/1.24 |
| 7,025,780 B2 | 4/2006 | Gabbay | 623/2.11 |
| 7,029,435 B2 * | 4/2006 | Nakao | 600/153 |
| 7,033,390 B2 | 4/2006 | Johnson et al. | 623/2.11 |
| 7,037,333 B2 | 5/2006 | Myers et al. | 623/2.13 |
| 7,037,334 B1 | 5/2006 | Hlavka et al. | 623/2.36 |
| 7,041,128 B2 | 5/2006 | McGuckin, Jr. et al. | 623/1.36 |
| 7,041,132 B2 | 5/2006 | Quijano et al. | 623/2.11 |
| 7,044,966 B2 | 5/2006 | Svanidze et al. | 623/2.1 |
| 7,044,967 B1 | 5/2006 | Solem et al. | 623/2.36 |
| 7,048,754 B2 | 5/2006 | Martin et al. | 606/232 |
| 7,048,757 B2 | 5/2006 | Shaknovich | 623/1.24 |
| 7,052,487 B2 | 5/2006 | Cohn et al. | 604/509 |
| 7,052,507 B2 | 5/2006 | Wakuda et al. | 606/194 |
| 7,063,722 B2 | 6/2006 | Marquez | 623/2.36 |
| 7,066,954 B2 | 6/2006 | Ryan et al. | 623/2.36 |
| 7,070,616 B2 | 7/2006 | Majercak et al. | 623/1.24 |
| 7,070,618 B2 | 7/2006 | Streeter | 623/2.36 |
| 7,077,862 B2 | 7/2006 | Vidlund et al. | 623/2.36 |
| 7,081,131 B2 | 7/2006 | Thornton | 623/1.24 |
| 7,087,064 B1 * | 8/2006 | Hyde | 606/142 |
| 7,089,051 B2 | 8/2006 | Jäverud et al. | 600/547 |
| 7,090,695 B2 | 8/2006 | Solem et al. | 623/2.37 |
| 7,166,127 B2 * | 1/2007 | Spence et al. | 623/2.37 |
| 2002/0013571 A1 | 1/2002 | Goldfarb et al. | 606/1 |
| 2002/0026216 A1 | 2/2002 | Grimes | 606/213 |
| 2002/0082630 A1 | 6/2002 | Menz et al. | 606/167 |
| 2002/0123802 A1 | 9/2002 | Snyders | 623/2.18 |
| 2002/0151970 A1 | 10/2002 | Garrison et al. | 623/2.11 |
| 2002/0183835 A1 | 12/2002 | Taylor et al. | 623/2.11 |
| 2002/0183838 A1 | 12/2002 | Taylor et al. | 623/2.11 |
| 2002/0198594 A1 | 12/2002 | Schreck | 623/2.11 |
| 2003/0050694 A1 | 3/2003 | Yang et al. | 623/2.11 |
| 2003/0130729 A1 | 7/2003 | Paniagua et al. | 623/2.11 |
| 2003/0163194 A1 | 8/2003 | Quijano et al. | 623/2.11 |
| 2003/0167071 A1 * | 9/2003 | Martin et al. | 606/232 |
| 2003/0171806 A1 | 9/2003 | Mathis et al. | 623/2.36 |
| 2003/0199975 A1 | 10/2003 | Gabbay | 623/2.36 |
| 2003/0229394 A1 | 12/2003 | Ogle et al. | 623/2.14 |
| 2003/0229395 A1 | 12/2003 | Cox | 623/2.36 |
| 2003/0233142 A1 | 12/2003 | Morales et al. | 623/2.37 |
| 2003/0236568 A1 | 12/2003 | Hojeibane et al. | 623/1.24 |
| 2003/0236569 A1 | 12/2003 | Mathis et al. | 623/1.26 |
| 2004/0002719 A1 | 1/2004 | Oz et al. | 606/142 |
| 2004/0003819 A1 | 1/2004 | St. Goar et al. | 128/898 |
| 2004/0010305 A1 | 1/2004 | Alferness et al. | 623/1.11 |
| 2004/0015230 A1 | 1/2004 | Moll et al. | 623/1.24 |
| 2004/0015232 A1 | 1/2004 | Shu et al. | 623/2.4 |
| 2004/0015233 A1 | 1/2004 | Jansen | 623/2.18 |
| 2004/0019374 A1 | 1/2004 | Hojeibane et al. | 623/1.13 |
| 2004/0019377 A1 | 1/2004 | Taylor et al. | 623/2.11 |
| 2004/0019378 A1 | 1/2004 | Hlavka et al. | 623/2.11 |
| 2004/0024447 A1 | 2/2004 | Haverich | 623/1.24 |
| 2004/0024451 A1 | 2/2004 | Johnson et al. | 623/2.11 |
| 2004/0024452 A1 | 2/2004 | Kruse et al. | 623/2.13 |
| 2004/0030321 A1 | 2/2004 | Fangrow, Jr. | 604/533 |
| 2004/0030381 A1 | 2/2004 | Shu | 623/2.11 |
| 2004/0030382 A1 | 2/2004 | St. Goar et al. | 623/2.36 |
| 2004/0030405 A1 | 2/2004 | Carpentier et al. | 623/23.72 |
| 2004/0034380 A1 | 2/2004 | Woolfson et al. | 606/170 |
| 2004/0034411 A1 | 2/2004 | Quijano et al. | 623/2.11 |
| 2004/0039436 A1 | 2/2004 | Spenser et al. | 623/1.13 |
| 2004/0039442 A1 | 2/2004 | St. Goar et al. | 623/2.36 |
| 2004/0039443 A1 | 2/2004 | Solem et al. | 623/2.37 |
| 2004/0044350 A1 | 3/2004 | Martin et al. | 606/139 |
| 2004/0044365 A1 | 3/2004 | Bachman | 606/213 |
| 2004/0044403 A1 | 3/2004 | Bischoff et al. | 623/1.41 |
| 2004/0049207 A1 | 3/2004 | Goldfarb et al. | 606/139 |
| 2004/0049211 A1 | 3/2004 | Tremulis et al. | 606/153 |
| 2004/0049266 A1 | 3/2004 | Anduiza et al. | 623/2.11 |
| 2004/0059351 A1 | 3/2004 | Eigler et al. | 606/148 |
| 2004/0059411 A1 | 3/2004 | Strecker | 623/1.23 |
| 2004/0059412 A1 | 3/2004 | Lytle, IV et al. | 623/2.11 |
| 2004/0060161 A1 | 4/2004 | Leal et al. | 29/558 |
| 2004/0073301 A1 | 4/2004 | Donlon et al. | 623/2.11 |
| 2004/0073302 A1 | 4/2004 | Rourke et al. | 623/2.36 |
| 2004/0078072 A1 | 4/2004 | Tu et al. | 623/1.23 |
| 2004/0078074 A1 | 4/2004 | Anderson et al. | 623/2.11 |
| 2004/0082910 A1 | 4/2004 | Constantz et al. | 604/101.04 |
| 2004/0082923 A1 | 4/2004 | Field | 604/267 |
| 2004/0082991 A1 | 4/2004 | Nguyen et al. | 623/2.14 |
| 2004/0087975 A1 | 5/2004 | Lucatero et al. | 606/139 |
| 2004/0088045 A1 | 5/2004 | Cox | 623/2.13 |
| 2004/0088046 A1 | 5/2004 | Speziali | 623/2.19 |
| 2004/0092858 A1 | 5/2004 | Wilson et al. | 604/9 |
| 2004/0093060 A1 | 5/2004 | Seguin et al. | 623/1.11 |
| 2004/0093070 A1 | 5/2004 | Hojeibane et al. | 623/1.15 |
| 2004/0093080 A1 | 5/2004 | Helmus et al. | 623/2.41 |
| 2004/0097979 A1 | 5/2004 | Svanidze et al. | 606/151 |
| 2004/0098098 A1 | 5/2004 | McGuckin, Jr. et al. | 623/1.14 |
| 2004/0098112 A1 | 5/2004 | DiMatteo et al. | 623/1.24 |
| 2004/0102839 A1 | 5/2004 | Cohn et al. | 623/2.11 |
| 2004/0102840 A1 | 5/2004 | Solem et al. | 623/2.11 |
| 2004/0102842 A1 | 5/2004 | Jansen | 623/2.38 |
| 2004/0106976 A1 | 6/2004 | Bailey et al. | 623/1.11 |
| 2004/0106990 A1 | 6/2004 | Spence et al. | 623/2.11 |
| 2004/0106991 A1 | 6/2004 | Hopkins et al. | 623/2.13 |
| 2004/0111096 A1 | 6/2004 | Tu et al. | 606/108 |
| 2004/0117009 A1 | 6/2004 | Cali et al. | 623/2.12 |
| 2004/0122448 A1 | 6/2004 | Levine | 606/139 |
| 2004/0122512 A1 | 6/2004 | Navia et al. | 623/2.12 |
| 2004/0122513 A1 | 6/2004 | Navia et al. | 623/2.12 |
| 2004/0122514 A1 | 6/2004 | Fogarty et al. | 623/2.14 |
| 2004/0122515 A1 | 6/2004 | Chu | 623/2.29 |
| 2004/0122516 A1 | 6/2004 | Fogarty et al. | 623/2.37 |
| 2004/0127979 A1 | 7/2004 | Wilson et al. | 623/2.1 |
| 2004/0127980 A1 | 7/2004 | Kowalsky et al. | 623/2.11 |
| 2004/0127981 A1 | 7/2004 | Rahdert et al. | 623/2.36 |
| 2004/0127982 A1 | 7/2004 | Machold et al. | 623/2.36 |
| 2004/0133220 A1 | 7/2004 | Lashinski et al. | 606/151 |
| 2004/0133267 A1 | 7/2004 | Lane | 623/1.24 |
| 2004/0133273 A1 | 7/2004 | Cox | 623/2.11 |
| 2004/0138742 A1 | 7/2004 | Myers et al. | 623/2.12 |
| 2004/0138743 A1 | 7/2004 | Myers et al. | 623/2.13 |
| 2004/0138744 A1 | 7/2004 | Lashinski et al. | 623/2.36 |
| 2004/0138745 A1 | 7/2004 | Macoviak et al. | 623/2.36 |
| 2004/0148018 A1 | 7/2004 | Carpentier et al. | 623/2.18 |
| 2004/0148019 A1 | 7/2004 | Vidlund et al. | 623/2.36 |

| Publication No. | Date | Inventor | Class |
|---|---|---|---|
| 2004/0148020 A1 | 7/2004 | Vidlund et al. | 623/2.36 |
| 2004/0153052 A1 | 8/2004 | Mathis | 606/1 |
| 2004/0153146 A1 | 8/2004 | Lashinski et al. | 623/2.11 |
| 2004/0153147 A1 | 8/2004 | Mathis | 623/2.37 |
| 2004/0158321 A1 | 8/2004 | Reuter et al. | 623/2.36 |
| 2004/0162610 A1 | 8/2004 | Liska et al. | 623/2.11 |
| 2004/0167539 A1 | 8/2004 | Kuehn et al. | 606/108 |
| 2004/0167620 A1 | 8/2004 | Ortiz et al. | 623/2.11 |
| 2004/0172046 A1 | 9/2004 | Hlavka et al. | 606/142 |
| 2004/0176839 A1 | 9/2004 | Huynh et al. | 623/2.4 |
| 2004/0176840 A1 | 9/2004 | Langberg et al. | 623/2.37 |
| 2004/0181238 A1 | 9/2004 | Zarbatany et al. | 606/108 |
| 2004/0186444 A1 | 9/2004 | Daly et al. | 604/247 |
| 2004/0186558 A1 | 9/2004 | Pavcnik et al. | 623/1.24 |
| 2004/0186561 A1 | 9/2004 | McGuckin, Jr. et al. | 623/1.36 |
| 2004/0186563 A1 | 9/2004 | Lobbi | 623/2.11 |
| 2004/0186565 A1 | 9/2004 | Schreck | 623/2.18 |
| 2004/0186566 A1 | 9/2004 | Hindrichs et al. | 623/2.37 |
| 2004/0193191 A1 | 9/2004 | Starksen et al. | 606/153 |
| 2004/0193253 A1 | 9/2004 | Thorpe et al. | 623/1.24 |
| 2004/0193260 A1 | 9/2004 | Alferness et al. | 623/2.11 |
| 2004/0199155 A1 | 10/2004 | Mollenauer | 606/27 |
| 2004/0199183 A1 | 10/2004 | Oz et al. | 606/142 |
| 2004/0199191 A1 | 10/2004 | Schwartz | 606/159 |
| 2004/0204758 A1 | 10/2004 | Eberhardt et al. | 623/2.15 |
| 2004/0206363 A1 | 10/2004 | McCarthy et al. | 128/898 |
| 2004/0210240 A1 | 10/2004 | Saint | 606/139 |
| 2004/0210301 A1 | 10/2004 | Obermiller | 623/1.24 |
| 2004/0210303 A1 | 10/2004 | Sedransk | 623/2.1 |
| 2004/0210304 A1 | 10/2004 | Seguin et al. | 623/2.11 |
| 2004/0210305 A1 | 10/2004 | Shu et al. | 623/2.11 |
| 2004/0210306 A1 | 10/2004 | Quijano et al. | 623/2.17 |
| 2004/0210307 A1 | 10/2004 | Khairkhahan | 623/2.18 |
| 2004/0215333 A1 | 10/2004 | Duran et al. | 623/1.24 |
| 2004/0215339 A1 | 10/2004 | Drasler et al. | 623/3.1 |
| 2004/0220654 A1 | 11/2004 | Mathis et al. | 623/1.11 |
| 2004/0220657 A1 | 11/2004 | Nieminen et al. | 623/1.15 |
| 2004/0225322 A1 | 11/2004 | Garrison et al. | 606/200 |
| 2004/0225344 A1 | 11/2004 | Hoffa et al. | 623/1.1 |
| 2004/0225348 A1 | 11/2004 | Case et al. | 623/1.15 |
| 2004/0225352 A1 | 11/2004 | Osborne et al. | 623/1.24 |
| 2004/0225353 A1 | 11/2004 | McGuckin, Jr. et al. | 623/2.11 |
| 2004/0225354 A1 | 11/2004 | Allen et al. | 623/2.11 |
| 2004/0225355 A1 | 11/2004 | Stevens | 623/2.11 |
| 2004/0225356 A1 | 11/2004 | Frater | 623/2.14 |
| 2004/0230117 A1 | 11/2004 | Tosaya et al. | 600/439 |
| 2004/0230297 A1 | 11/2004 | Thornton | 623/1.24 |
| 2004/0236411 A1 | 11/2004 | Sarac et al. | 623/1.26 |
| 2004/0236418 A1 | 11/2004 | Stevens | 623/2.11 |
| 2004/0236419 A1 | 11/2004 | Milo | 623/2.36 |
| 2004/0243153 A1 | 12/2004 | Liddicoat et al. | 606/151 |
| 2004/0243219 A1 | 12/2004 | Fischer et al. | 623/1.15 |
| 2004/0243227 A1 | 12/2004 | Starksen et al. | 623/2.11 |
| 2004/0243228 A1 | 12/2004 | Kowalsky et al. | 623/2.11 |
| 2004/0243230 A1 | 12/2004 | Navia et al. | 623/2.36 |
| 2004/0254600 A1 | 12/2004 | Zarbatany et al. | 606/194 |
| 2004/0254636 A1 | 12/2004 | Flagle et al. | 623/1.24 |
| 2004/0260276 A1 | 12/2004 | Rudko et al. | 606/15 |
| 2004/0260317 A1 | 12/2004 | Bloom et al. | 606/151 |
| 2004/0260322 A1 | 12/2004 | Rudko et al. | 606/167 |
| 2004/0260389 A1 | 12/2004 | Case et al. | 623/1.24 |
| 2004/0260390 A1 | 12/2004 | Sarac et al. | 623/1.24 |
| 2004/0260393 A1 | 12/2004 | Rahdert et al. | 623/2.36 |
| 2004/0260394 A1 | 12/2004 | Douk et al. | 623/2.36 |
| 2004/0267357 A1 | 12/2004 | Allen et al. | 623/2.11 |
| 2005/0004583 A1 | 1/2005 | Oz et al. | 606/142 |
| 2005/0004667 A1 | 1/2005 | Swinford et al. | 623/2.36 |
| 2005/0010285 A1 | 1/2005 | Lambrecht et al. | 623/2.18 |
| 2005/0010287 A1 | 1/2005 | Macoviak et al. | 623/2.36 |
| 2005/0015112 A1 | 1/2005 | Cohn et al. | 606/200 |
| 2005/0021056 A1 | 1/2005 | St. Goar et al. | 606/144 |
| 2005/0021136 A1 | 1/2005 | Xie et al. | 623/2.14 |
| 2005/0027261 A1 | 2/2005 | Weaver et al. | 604/246 |
| 2005/0027348 A1 | 2/2005 | Case et al. | 623/1.24 |
| 2005/0027351 A1 | 2/2005 | Reuter et al. | 623/2.11 |
| 2005/0027353 A1 | 2/2005 | Alferness et al. | 623/2.11 |
| 2005/0033398 A1 | 2/2005 | Seguin | 623/1.11 |
| 2005/0033419 A1 | 2/2005 | Alferness et al. | 623/2.11 |
| 2005/0033446 A1 | 2/2005 | Deem et al. | 623/23.6 |
| 2005/0038506 A1 | 2/2005 | Webler et al. | 623/2.11 |
| 2005/0038507 A1 | 2/2005 | Alferness et al. | 623/2.11 |
| 2005/0043790 A1 | 2/2005 | Seguin | 623/2.18 |
| 2005/0043792 A1 | 2/2005 | Solem et al. | 623/2.36 |
| 2005/0049679 A1 | 3/2005 | Taylor et al. | 623/1.15 |
| 2005/0049692 A1 | 3/2005 | Numamoto et al. | 623/1.24 |
| 2005/0049696 A1 | 3/2005 | Siess et al. | 623/2.11 |
| 2005/0049697 A1 | 3/2005 | Sievers | 623/2.26 |
| 2005/0054977 A1 | 3/2005 | Laird et al. | 604/96.01 |
| 2005/0055079 A1 | 3/2005 | Duran | 623/1.13 |
| 2005/0055087 A1 | 3/2005 | Starksen | 623/2.11 |
| 2005/0055088 A1 | 3/2005 | Liddicoat et al. | 623/2.11 |
| 2005/0055089 A1 | 3/2005 | Macoviak et al. | 623/2.37 |
| 2005/0060029 A1 | 3/2005 | Le et al. | 623/2.11 |
| 2005/0060030 A1 | 3/2005 | Lashinski et al. | 623/2.37 |
| 2005/0065460 A1 | 3/2005 | Laird | 604/20 |
| 2005/0065550 A1 | 3/2005 | Starksen et al. | 606/219 |
| 2005/0065594 A1 | 3/2005 | Dimatteo et al. | 623/1.24 |
| 2005/0065597 A1 | 3/2005 | Lansac | 623/2.11 |
| 2005/0070998 A1 | 3/2005 | Rourke et al. | 623/2.11 |
| 2005/0075584 A1 | 4/2005 | Cali | 600/587 |
| 2005/0075659 A1 | 4/2005 | Realyvasquez et al. | 606/167 |
| 2005/0075662 A1 | 4/2005 | Pedersen et al. | 606/194 |
| 2005/0075712 A1 | 4/2005 | Biancucci et al. | 623/1.11 |
| 2005/0075713 A1 | 4/2005 | Biancucci et al. | 623/1.11 |
| 2005/0075717 A1 | 4/2005 | Nguyen et al. | 623/1.26 |
| 2005/0075718 A1 | 4/2005 | Nguyen et al. | 623/1.26 |
| 2005/0075719 A1 | 4/2005 | Bergheim | 623/1.26 |
| 2005/0075720 A1 | 4/2005 | Nguyen et al. | 623/1.26 |
| 2005/0075723 A1 | 4/2005 | Schroeder et al. | 623/2.1 |
| 2005/0075724 A1 | 4/2005 | Svanidze et al. | 623/2.11 |
| 2005/0075725 A1 | 4/2005 | Rowe | 623/2.14 |
| 2005/0075726 A1 | 4/2005 | Svanidze et al. | 623/2.14 |
| 2005/0075728 A1 | 4/2005 | Nguyen et al. | 623/2.17 |
| 2005/0075729 A1 | 4/2005 | Nguyen et al. | 623/2.18 |
| 2005/0075730 A1 | 4/2005 | Myers et al. | 623/2.18 |
| 2005/0075731 A1 | 4/2005 | Artof et al. | 623/2.18 |
| 2005/0080483 A1 | 4/2005 | Solem et al. | 623/2.11 |
| 2005/0085900 A1 | 4/2005 | Case et al. | 623/1.24 |
| 2005/0085903 A1 | 4/2005 | Lau | 623/2.11 |
| 2005/0085904 A1 | 4/2005 | Lemmon | 623/2.11 |
| 2005/0090846 A1 | 4/2005 | Pedersen et al. | 606/159 |
| 2005/0096735 A1 | 5/2005 | Hojeibane et al. | 623/1.24 |
| 2005/0096738 A1 | 5/2005 | Cali et al. | 623/2.18 |
| 2005/0096739 A1 | 5/2005 | Cao | 623/2.19 |
| 2005/0096740 A1 | 5/2005 | Langberg et al. | 623/2.36 |
| 2005/0101975 A1 | 5/2005 | Nguyen et al. | 606/151 |
| 2005/0102026 A1 | 5/2005 | Turner et al. | 623/2.1 |
| 2005/0107810 A1 | 5/2005 | Morales et al. | 606/143 |
| 2005/0107811 A1 | 5/2005 | Starksen et al. | 606/143 |
| 2005/0107812 A1 | 5/2005 | Starksen et al. | 606/143 |
| 2005/0107872 A1 | 5/2005 | Mensah et al. | 623/2.14 |
| 2005/0113910 A1 | 5/2005 | Paniagua et al. | 623/2.14 |
| 2005/0119673 A1 | 6/2005 | Gordon et al. | 606/151 |
| 2005/0119734 A1 | 6/2005 | Spence et al. | 623/2.11 |
| 2005/0119735 A1 | 6/2005 | Spence et al. | 623/2.36 |
| 2005/0125011 A1 | 6/2005 | Spence et al. | 606/144 |
| 2005/0131438 A1 | 6/2005 | Cohn | 606/170 |
| 2005/0137449 A1 | 6/2005 | Nieminen et al. | 600/37 |
| 2005/0137450 A1 | 6/2005 | Aronson et al. | 600/37 |
| 2005/0137451 A1 | 6/2005 | Gordon et al. | 600/37 |
| 2005/0137676 A1 | 6/2005 | Richardson et al. | 623/1.11 |
| 2005/0137681 A1 | 6/2005 | Shoemaker et al. | 623/1.23 |
| 2005/0137682 A1 | 6/2005 | Justino | 623/1.24 |
| 2005/0137685 A1 | 6/2005 | Nieminen et al. | 623/2.11 |
| 2005/0137686 A1 | 6/2005 | Salahieh et al. | 623/2.11 |
| 2005/0137688 A1 | 6/2005 | Salahieh et al. | 623/2.11 |

| Publication No. | Date | Inventor | Class |
|---|---|---|---|
| 2005/0137689 A1 | 6/2005 | Salahieh et al. | 623/2.11 |
| 2005/0137690 A1 | 6/2005 | Salahieh et al. | 623/2.11 |
| 2005/0137691 A1 | 6/2005 | Salahieh et al. | 623/2.11 |
| 2005/0137692 A1 | 6/2005 | Haug et al. | 623/2.11 |
| 2005/0137693 A1 | 6/2005 | Haug et al. | 623/2.11 |
| 2005/0137694 A1 | 6/2005 | Haug et al. | 623/2.11 |
| 2005/0137696 A1 | 6/2005 | Salahieh et al. | 623/2.11 |
| 2005/0137697 A1 | 6/2005 | Salahieh et al. | 623/2.11 |
| 2005/0137698 A1 | 6/2005 | Salahieh et al. | 623/2.11 |
| 2005/0137699 A1 | 6/2005 | Salahieh et al. | 623/2.11 |
| 2005/0137700 A1 | 6/2005 | Spence et al. | 623/2.36 |
| 2005/0137701 A1 | 6/2005 | Salahieh et al. | 623/2.38 |
| 2005/0137702 A1 | 6/2005 | Haug et al. | 623/2.38 |
| 2005/0143807 A1 | 6/2005 | Pavcnik et al. | 623/1.24 |
| 2005/0143809 A1 | 6/2005 | Salahieh et al. | 623/2.11 |
| 2005/0143810 A1 | 6/2005 | Dauner et al. | 623/2.12 |
| 2005/0143811 A1 | 6/2005 | Realyvasquez | 623/2.36 |
| 2005/0149014 A1 | 7/2005 | Hauck et al. | 606/41 |
| 2005/0149179 A1 | 7/2005 | Mathis et al. | 623/2.11 |
| 2005/0149180 A1 | 7/2005 | Mathis et al. | 623/2.11 |
| 2005/0149181 A1 | 7/2005 | Eberhardt | 623/2.14 |
| 2005/0159810 A1 | 7/2005 | Filsoufi | 623/2.1 |
| 2005/0159811 A1 | 7/2005 | Lane | 623/2.14 |
| 2005/0165477 A1 | 7/2005 | Anduiza et al. | 623/2.11 |
| 2005/0165478 A1 | 7/2005 | Song | 623/2.22 |
| 2005/0171472 A1 | 8/2005 | Lutter | 604/101.03 |
| 2005/0171601 A1 | 8/2005 | Cosgrove et al. | 623/2.11 |
| 2005/0177227 A1 | 8/2005 | Heim et al. | 623/2.12 |
| 2005/0177228 A1 | 8/2005 | Solem et al. | 623/2.36 |
| 2005/0182483 A1 | 8/2005 | Osborne et al. | 623/1.24 |
| 2005/0184122 A1 | 8/2005 | Hlavka et al. | 227/175.1 |
| 2005/0187614 A1 | 8/2005 | Agnew | 623/1.24 |
| 2005/0187616 A1 | 8/2005 | Realyvasquez | 623/2.11 |
| 2005/0187617 A1 | 8/2005 | Navia | 623/2.13 |
| 2005/0192606 A1 | 9/2005 | Paul, Jr. et al. | 606/159 |
| 2005/0192665 A1 | 9/2005 | Spenser et al. | 623/2.11 |
| 2005/0197692 A1 | 9/2005 | Pai et al. | 623/2.1 |
| 2005/0197693 A1 | 9/2005 | Pai et al. | 623/2.1 |
| 2005/0197694 A1 | 9/2005 | Pai et al. | 623/2.1 |
| 2005/0203549 A1 | 9/2005 | Realyvasquez | 606/142 |
| 2005/0203605 A1 | 9/2005 | Dolan | 623/1.11 |
| 2005/0203614 A1 | 9/2005 | Forster et al. | 623/2.11 |
| 2005/0203615 A1 | 9/2005 | Forster et al. | 623/2.11 |
| 2005/0203616 A1 | 9/2005 | Cribier | 623/2.1 |
| 2005/0203617 A1 | 9/2005 | Forster et al. | 623/2.14 |
| 2005/0203618 A1 | 9/2005 | Sharkawy et al. | 623/2.38 |
| 2005/0216039 A1 | 9/2005 | Lederman | 606/144 |
| 2005/0216077 A1 | 9/2005 | Mathis et al. | 623/2.11 |
| 2005/0216078 A1 | 9/2005 | Starksen et al. | 623/2.11 |
| 2005/0222675 A1 | 10/2005 | Sauter | 623/1.26 |
| 2005/0222678 A1 | 10/2005 | Lashinski et al. | 623/2.1 |
| 2005/0228422 A1 | 10/2005 | Machold et al. | 606/167 |
| 2005/0228479 A1 | 10/2005 | Pavcnik et al. | 623/1.11 |
| 2005/0228486 A1 | 10/2005 | Case et al. | 623/1.24 |
| 2005/0228494 A1 | 10/2005 | Marquez | 623/2.18 |
| 2005/0228495 A1 | 10/2005 | Macoviak | 623/2.18 |
| 2005/0228496 A1 | 10/2005 | Mensah et al. | 623/2.41 |
| 2005/0234541 A1 | 10/2005 | Hunt et al. | 623/1.24 |
| 2005/0234546 A1 | 10/2005 | Nugent et al. | 623/2.11 |
| 2005/0240200 A1 | 10/2005 | Bergheim | 606/108 |
| 2005/0240202 A1 | 10/2005 | Shennib et al. | 606/142 |
| 2005/0240255 A1 | 10/2005 | Schaeffer | 623/1.11 |
| 2005/0240259 A1 | 10/2005 | Sisken et al. | 623/1.36 |
| 2005/0240262 A1 | 10/2005 | White | 623/2.12 |
| 2005/0244460 A1 | 10/2005 | Alferiev et al. | 424/426 |
| 2005/0246013 A1 | 11/2005 | Gabbay | 623/2.1 |
| 2005/0251251 A1 | 11/2005 | Cribier | 623/2.11 |
| 2005/0256566 A1 | 11/2005 | Gabbay | 623/2.1 |
| 2005/0261704 A1 | 11/2005 | Mathis | 606/108 |
| 2005/0261759 A1 | 11/2005 | Lambrecht et al. | 623/1.26 |
| 2005/0267493 A1 | 12/2005 | Schreck et al. | 606/139 |
| 2005/0267560 A1 | 12/2005 | Bates | 623/1.1 |
| 2005/0267565 A1 | 12/2005 | Dave et al. | 623/1.15 |
| 2005/0267571 A1 | 12/2005 | Spence et al. | 623/2.11 |
| 2005/0267573 A9 | 12/2005 | Macoviak et al. | 623/2.36 |
| 2005/0267574 A1 | 12/2005 | Cohn et al. | |
| 2005/0272969 A1 | 12/2005 | Alferness et al. | 600/37 |
| 2005/0273160 A1 | 12/2005 | Lashinski et al. | 623/1.25 |
| 2005/0278015 A1 | 12/2005 | Dave et al. | 623/1.38 |
| 2005/0283178 A1 | 12/2005 | Flagle et al. | 606/191 |
| 2005/0288779 A1 | 12/2005 | Shaoulian et al. | 623/2.37 |
| 2006/0000715 A1 | 1/2006 | Whitcher et al. | 205/80 |
| 2006/0004439 A1 | 1/2006 | Spenser et al. | 623/1.23 |
| 2006/0004442 A1 | 1/2006 | Spenser et al. | 623/2.11 |
| 2006/0009804 A1 | 1/2006 | Pederson | 607/2 |
| 2006/0009841 A1 | 1/2006 | McGuckin, Jr. et al. | 623/2.38 |
| 2006/0009842 A1 | 1/2006 | Huynh et al. | 623/2.41 |
| 2006/0013805 A1 | 1/2006 | Hebbel et al. | 424/93.21 |
| 2006/0013855 A1 | 1/2006 | Carpenter et al. | 424/423 |
| 2006/0015136 A1 | 1/2006 | Besselink | 606/200 |
| 2006/0015178 A1 | 1/2006 | Moaddeb et al. | 623/2.36 |
| 2006/0015179 A1 | 1/2006 | Bulman-Fleming et al. | 623/2.36 |
| 2006/0020275 A1 | 1/2006 | Goldfarb et al. | 606/151 |
| 2006/0020327 A1 | 1/2006 | Lashinski et al. | 623/1.25 |
| 2006/0020332 A1 | 1/2006 | Lashinski et al. | 623/2.11 |
| 2006/0020334 A1 | 1/2006 | Lashinski et al. | 623/2.11 |
| 2006/0020335 A1 | 1/2006 | Kowalsky et al. | 623/2.36 |
| 2006/0020336 A1 | 1/2006 | Liddicoat | |
| 2006/0025750 A1 | 2/2006 | Startksen et al. | 604/510 |
| 2006/0025784 A1 | 2/2006 | Startksen et al. | 606/151 |
| 2006/0025787 A1 | 2/2006 | Morales et al. | 606/151 |
| 2006/0025854 A1 | 2/2006 | Lashinski et al. | 623/1.25 |
| 2006/0025855 A1 | 2/2006 | Lashinski et al. | 623/2.1 |
| 2006/0025856 A1 | 2/2006 | Ryan et al. | 623/2.11 |
| 2006/0025857 A1 | 2/2006 | Bergheim et al. | 623/2.18 |
| 2006/0030747 A1 | 2/2006 | Kantrowitz et al. | 600/16 |
| 2006/0030866 A1 | 2/2006 | Schreck | 606/139 |
| 2006/0030882 A1 | 2/2006 | Adams et al. | |
| 2006/0030885 A1 | 2/2006 | Hyde | 606/232 |
| 2006/0036317 A1 | 2/2006 | Vidlund et al. | 623/2.36 |
| 2006/0041305 A1 | 2/2006 | Lauterjung | 623/1.36 |
| 2006/0041306 A1 | 2/2006 | Vidlund et al. | 623/2.11 |
| 2006/0047297 A1 | 3/2006 | Case | 606/194 |
| 2006/0047338 A1 | 3/2006 | Jenson | 623/2.11 |
| 2006/0047343 A1 | 3/2006 | Oviatt et al. | 623/915 |
| 2006/0052804 A1 | 3/2006 | Mialhe | 606/157 |
| 2006/0052867 A1 | 3/2006 | Revuelta et al. | 623/2.18 |
| 2006/0058817 A1 | 3/2006 | Starksen et al. | 606/142 |
| 2006/0058865 A1 | 3/2006 | Case et al. | 623/1.11 |
| 2006/0058871 A1 | 3/2006 | Zakay et al. | |
| 2006/0058889 A1 | 3/2006 | Case et al. | 623/23.68 |
| 2006/0064115 A1 | 3/2006 | Allen et al. | 606/139 |
| 2006/0064116 A1 | 3/2006 | Allen et al. | 606/139 |
| 2006/0064118 A1 | 3/2006 | Kimblad | 606/151 |
| 2006/0064174 A1 | 3/2006 | Zadno | 623/23.68 |
| 2006/0069400 A1 | 3/2006 | Burnett et al. | 606/153 |
| 2006/0069429 A1 | 3/2006 | Spence et al. | 623/2.11 |
| 2006/0069430 A9 | 3/2006 | Rahdert et al. | 623/2.36 |
| 2006/0074483 A1 | 4/2006 | Schrayer | 623/2.1 |
| 2006/0074484 A1 | 4/2006 | Huber | 623/2.1 |
| 2006/0074485 A1 | 4/2006 | Realyvasquez | 623/2.11 |
| 2006/0085060 A1 | 4/2006 | Campbell | 623/1.26 |
| 2006/0089708 A1 | 4/2006 | Osse et al. | 623/1.24 |
| 2006/0095115 A1 | 5/2006 | Bladillah et al. | 623/1.16 |
| 2006/0095125 A1 | 5/2006 | Chinn et al. | 623/2.4 |
| 2006/0099326 A1 | 5/2006 | Keogh et al. | 427/2.36 |
| 2006/0100697 A1 | 5/2006 | Casanova | 623/2.36 |
| 2006/0100699 A1 | 5/2006 | Vidlund et al. | 623/2.36 |
| 2006/0106278 A1 | 5/2006 | Machold et al. | 600/37 |
| 2006/0106279 A1 | 5/2006 | Machold et al. | 600/37 |
| 2006/0106456 A9 | 5/2006 | Machold et al. | 623/2.36 |
| 2006/0111660 A1 | 5/2006 | Wolf et al. | 604/9 |
| 2006/0111773 A1 | 5/2006 | Rittgers et al. | 623/1.24 |
| 2006/0111774 A1 | 5/2006 | Samkov et al. | 623/2.25 |
| 2006/0116572 A1 | 6/2006 | Case | 600/424 |

| | | | |
|---|---|---|---|
| 2006/0116756 A1 | 6/2006 | Solem et al. ............... 623/2.11 |
| 2006/0122686 A1 | 6/2006 | Gilad et al. ................ 623/1.13 |
| 2006/0122692 A1 | 6/2006 | Gilad et al. ................ 623/1.24 |
| 2006/0122693 A1 | 6/2006 | Biadillah et al. ........... 623/1.24 |
| 2006/0127443 A1 | 6/2006 | Helmus ...................... 424/423 |
| 2006/0129235 A1 | 6/2006 | Seguin et al. .............. 623/2.11 |
| 2006/0129236 A1 | 6/2006 | McCarthy .................. 623/2.36 |
| 2006/0135476 A1 | 6/2006 | Kutryk et al. ................. 514/59 |
| 2006/0135964 A1 | 6/2006 | Vesely ........................ 606/108 |
| 2006/0135967 A1 | 6/2006 | Realyvasquez ............. 606/142 |
| 2006/0136044 A1 | 6/2006 | Osborne ..................... 623/1.24 |
| 2006/0136045 A1 | 6/2006 | Flagle et al. ............... 623/1.24 |
| 2006/0136052 A1 | 6/2006 | Vesely ....................... 623/2.18 |
| 2006/0136054 A1 | 6/2006 | Berg et al. ................. 623/2.38 |
| 2006/0142846 A1 | 6/2006 | Pavcnik et al. ............. 623/1.24 |
| 2006/0142847 A1 | 6/2006 | Shaknovich ............... 623/1.24 |
| 2006/0142848 A1 | 6/2006 | Gabbay ...................... 623/1.26 |
| 2006/0142854 A1 | 6/2006 | Alferness et al. ........... 623/2.11 |
| 2006/0149358 A1 | 7/2006 | Zilla et al. ................. 623/1.22 |
| 2006/0149360 A1 | 7/2006 | Schwammenthal et al. 623/1.24 |
| 2006/0149367 A1 | 7/2006 | Sieracki ..................... 623/2.21 |
| 2006/0149368 A1 | 7/2006 | Spence ...................... 623/2.37 |
| 2006/0161133 A1 | 7/2006 | Laird et al. ................. 604/509 |
| 2006/0161248 A1 | 7/2006 | Case et al. .................... 623/2.1 |
| 2006/0161249 A1 | 7/2006 | Realyvasquez et al. .... 623/2.11 |
| 2006/0161250 A1 | 7/2006 | Shaw ........................ 623/2.17 |
| 2006/0167468 A1 | 7/2006 | Gabbay ...................... 606/108 |
| 2006/0167541 A1 | 7/2006 | Lattouf ...................... 623/2.11 |
| 2006/0167542 A1 | 7/2006 | Quintessenza ............. 623/2.12 |
| 2006/0167543 A1 | 7/2006 | Bailey et al. ............... 623/2.18 |

FOREIGN PATENT DOCUMENTS

| | | |
|---|---|---|
| EP | 0 466 518 | 1/1992 |
| EP | 0769272 A1 | 4/1997 |
| FR | 2 728 457 | 6/1996 |
| WO | WO 88/00459 | 1/1988 |
| WO | WO 90/15582 | 12/1990 |
| WO | WO 94/03227 A1 | 2/1994 |
| WO | WO 95/01669 | 1/1995 |
| WO | WO 96/19159 | 6/1996 |
| WO | WO 98/46115 | 10/1998 |
| WO | WO 99/04724 | 2/1999 |
| WO | WO 00/03759 A2 | 1/2000 |
| WO | WO 00/60995 A2 | 10/2000 |
| WO | WO 00/67679 | 11/2000 |
| WO | WO 01/15650 | 3/2001 |
| WO | WO 01/17462 | 3/2001 |
| WO | WO 01/28432 A1 | 4/2001 |
| WO | WO 03/047468 | 6/2003 |
| WO | WO 03/084443 | 10/2003 |
| WO | WO 2004/012583 | 2/2004 |
| WO | WO 2004/019825 | 3/2004 |
| WO | WO 2004/021893 | 3/2004 |
| WO | WO 2004/023980 | 3/2004 |
| WO | WO 2004/030568 | 4/2004 |
| WO | WO 2004/030569 | 4/2004 |
| WO | WO 2004/030570 | 4/2004 |
| WO | WO 2004/032724 | 4/2004 |
| WO | WO 2004/032796 | 4/2004 |
| WO | WO 2004/037128 | 5/2004 |
| WO | WO 2004/037317 | 5/2004 |
| WO | WO 2004/039432 | 5/2004 |
| WO | WO 2004/043265 | 5/2004 |
| WO | WO 2004/043273 | 5/2004 |
| WO | WO 2004/043293 | 5/2004 |
| WO | WO 2004/045370 | 6/2004 |
| WO | WO 2004/045378 | 6/2004 |
| WO | WO 2004/045463 | 6/2004 |
| WO | WO 2004/047677 | 6/2004 |
| WO | WO 2004/060217 | 7/2004 |
| WO | WO 2004/060470 | 7/2004 |
| WO | WO 2004/062725 | 7/2004 |
| WO | WO 2004/066803 | 8/2004 |
| WO | WO 2004/066826 | 8/2004 |
| WO | WO 2004/069287 | 8/2004 |
| WO | WO 2004/075789 | 9/2004 |
| WO | WO 2004/080352 | 9/2004 |
| WO | WO 2004/082523 | 9/2004 |
| WO | WO 2004/082527 | 9/2004 |
| WO | WO 2004/082528 | 9/2004 |
| WO | WO 2004/082536 | 9/2004 |
| WO | WO 2004/082537 | 9/2004 |
| WO | WO 2004/082538 | 9/2004 |
| WO | WO 2004/082757 | 9/2004 |
| WO | WO 2004/084746 | 10/2004 |
| WO | WO 2004/084770 | 10/2004 |
| WO | WO 2004/089246 | 10/2004 |
| WO | WO 2004/089250 | 10/2004 |
| WO | WO 2004/089253 | 10/2004 |
| WO | WO 2004/091449 | 10/2004 |
| WO | WO 2004/091454 | 10/2004 |
| WO | WO 2004/093638 | 11/2004 |
| WO | WO 2004/093726 | 11/2004 |
| WO | WO 2004/093728 | 11/2004 |
| WO | WO 2004/093730 | 11/2004 |
| WO | WO 2004/093745 | 11/2004 |
| WO | WO 2004/093935 | 11/2004 |
| WO | WO 2004/096100 | 11/2004 |
| WO | WO 2004/103222 | 12/2004 |
| WO | WO 2004/103223 | 12/2004 |
| WO | WO 2004/105584 | 12/2004 |
| WO | WO 2004/105651 | 12/2004 |
| WO | WO 2004/112582 | 12/2004 |
| WO | WO 2004/112585 | 12/2004 |
| WO | WO 2004/112643 | 12/2004 |
| WO | WO 2004/112652 | 12/2004 |
| WO | WO 2004/112657 | 12/2004 |
| WO | WO 2004/112658 | 12/2004 |
| WO | WO 2005/000152 | 1/2005 |
| WO | WO 2005/002424 | 1/2005 |
| WO | WO 2005/002466 | 1/2005 |
| WO | WO 2005/004753 | 1/2005 |
| WO | WO 2005/007017 | 1/2005 |
| WO | WO 2005/007018 | 1/2005 |
| WO | WO 2005/007036 | 1/2005 |
| WO | WO 2005/007037 | 1/2005 |
| WO | WO 2005/009285 | 2/2005 |
| WO | WO 2005/009286 | 2/2005 |
| WO | WO 2005/009505 | 2/2005 |
| WO | WO 2005/009506 | 2/2005 |
| WO | WO 2005/011473 | 2/2005 |
| WO | WO 2005/011534 | 2/2005 |
| WO | WO 2005/011535 | 2/2005 |
| WO | WO 2005/013860 | 2/2005 |
| WO | WO 2005/018507 | 3/2005 |
| WO | WO 2005/021063 | 3/2005 |
| WO | WO 2005/023155 | 3/2005 |
| WO | WO 2005/025644 | 3/2005 |
| WO | WO 2005/027790 | 3/2005 |
| WO | WO 2005/027797 | 3/2005 |
| WO | WO 2005/034812 | 4/2005 |
| WO | WO 2005/039428 | 5/2005 |
| WO | WO 2005/039452 | 5/2005 |
| WO | WO 2005/046488 | 5/2005 |
| WO | WO 2005/046528 | 5/2005 |
| WO | WO 2005/046529 | 5/2005 |
| WO | WO 2005/046530 | 5/2005 |
| WO | WO 2005/046531 | 5/2005 |
| WO | WO 2005/048883 | 6/2005 |
| WO | WO 2005/049103 | 6/2005 |
| WO | WO 2005/051226 | 6/2005 |
| WO | WO 2005/055811 | 6/2005 |
| WO | WO 2005/055883 | 6/2005 |
| WO | WO 2005/058206 | 6/2005 |
| WO | WO 2005/065585 | 7/2005 |

| | | |
|---|---|---|
| WO | WO 2005/065593 | 7/2005 |
| WO | WO 2005/065594 | 7/2005 |
| WO | WO 2005/070342 | 8/2005 |
| WO | WO 2005/070343 | 8/2005 |
| WO | WO 2005/072654 | 8/2005 |
| WO | WO 2005/072655 | 8/2005 |
| WO | WO 2005/079706 | 9/2005 |
| WO | WO 2005/082288 | 9/2005 |
| WO | WO 2005/082289 | 9/2005 |
| WO | WO 2005/084595 | 9/2005 |
| WO | WO 2005/087139 | 9/2005 |
| WO | WO 2005/087140 | 9/2005 |
| WO | WO 2006/000763 | 1/2006 |
| WO | WO 2006/000776 | 1/2006 |
| WO | WO 2006/002492 | 1/2006 |
| WO | WO 2006/004679 | 1/2006 |
| WO | WO 2006/005015 | 1/2006 |
| WO | WO 2006/009690 | 1/2006 |
| WO | WO 2006/011127 | 2/2006 |
| WO | WO 2006/012011 | 2/2006 |
| WO | WO 2006/012013 | 2/2006 |
| WO | WO 2006/012038 | 2/2006 |
| WO | WO 2006/012068 | 2/2006 |
| WO | WO 2006/012322 | 2/2006 |
| WO | WO 2006/019498 | 2/2006 |
| WO | WO 2006/026371 | 3/2006 |
| WO | WO 2006/026377 | 3/2006 |
| WO | WO 2006/026912 | 3/2006 |
| WO | WO 2006/027499 | 3/2006 |
| WO | WO 2006/028821 | 3/2006 |
| WO | WO 2006/029062 | 3/2006 |
| WO | WO 2006/031436 | 3/2006 |
| WO | WO 2006/031469 | 3/2006 |
| WO | WO 2006/032051 | 3/2006 |
| WO | WO 2006/034245 | 3/2006 |
| WO | WO 2006/035415 | 4/2006 |
| WO | WO 2006/041505 | 4/2006 |
| WO | WO 2006/044679 | 4/2006 |
| WO | WO 2006/048664 | 5/2006 |
| WO | WO 2006/050459 | 5/2006 |
| WO | WO 2006/050460 | 5/2006 |
| WO | WO 2006/054107 | 5/2006 |
| WO | WO 2006/054930 | 5/2006 |
| WO | WO 2006/055982 | 5/2006 |
| WO | WO 2006/060546 | 6/2006 |
| WO | WO 2006/063108 | 6/2006 |
| WO | WO 2006/063181 | 6/2006 |
| WO | WO 2006/063199 | 6/2006 |
| WO | WO 2006/064490 | 6/2006 |
| WO | WO 2006/065212 | 6/2006 |
| WO | WO 2006/065930 | 6/2006 |
| WO | WO 2006/066148 | 6/2006 |
| WO | WO 2006/066150 | 6/2006 |
| WO | WO 2006/069094 | 6/2006 |
| WO | WO 2006/070372 | 7/2006 |
| WO | WO 2006/073628 | 7/2006 |
| WO | WO 2006/076890 | 7/2006 |

\* cited by examiner

US 7,799,038 B2

TRANSLUMENAL APPARATUS, SYSTEM, AND METHOD

FIELD OF THE INVENTION

The present invention relates generally to apparatus, systems, and methods for use in a heart, more particularly to apparatus, systems, and methods for improving the function of a heart valve.

BACKGROUND

The human heart is divided into four chambers. These four chambers include the right atrium and the right ventricle, and the left atrium and the left ventricle. The heart contracts rhythmically under stimulation of electrical currents to move blood through the chambers of the heart and the remainder of the cardiovascular system.

Blood in the heart is kept flowing in a unidirectional manner through the cardiovascular system by a system of four one-way valves. As the heart cycles the valves open and close to allow blood to move one-way through the heart chambers.

The heart valves differ significantly in structure. For example, the ventricles are separated from the atria by valves that, in addition to the leaflets, have thin but strong cords of fibrous tissue. Called chordae tendineae, these cords tether the valve to the ventricular walls. When the ventricles contract, small muscles in their walls, called papillary muscles, pull the cords which act as tethers, and control the closure of the valve leaflets, preventing them from flapping too far backwards.

One such valve located between the left ventricle and the left atrium is called the mitral valve. The mitral valve has two leaflets that form the valve. The leaflets are attached to papillary muscles by way of the chordae tendineae and it allows blood to enter the left ventricle from the left atrium.

When operating properly, the mitral valve acts as a one-way valve. There are, however, numerous conditions that can cause the mitral valve to not act as a one-way valve. For example, deficiency or degeneration of one or more of the mitral valve structures may result in dysfunction of the mitral valve apparatus leading to mitral valve prolapse or regurgitation during a contraction of the heart. Prolapse or regurgitation of the mitral valve can eventually lead to severe cardiovascular problems, and even death.

DETAILED DESCRIPTION

Figure 1:
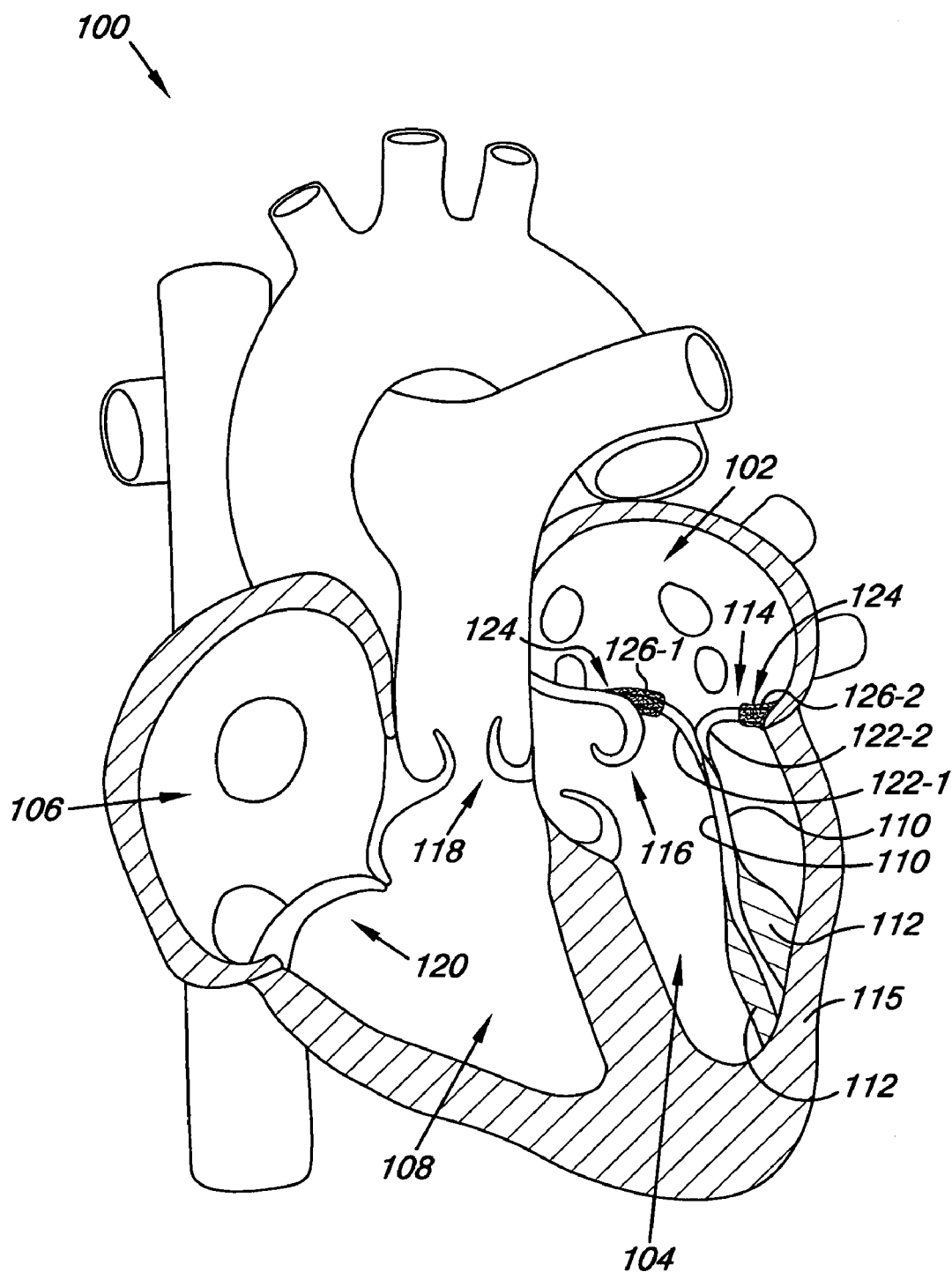
FIG. 1 provides a schematic cross-section of a heart, segments of which have been removed to show detail.

Embodiments of the present invention are directed to methods, apparatus, and systems for helping to improve heart valve function. As discussed herein, improving heart valve function can be accomplished by altering the configuration of the heart valve according to various embodiments of the invention. For example, altering the configuration of the heart valve can be accomplished through the use of a cord delivered into the heart by a delivery catheter. The cord can be positioned relative the heart valve in such a way that by manipulating aspects of the cord (e.g., its length) the configuration of the heart valve can be alter so as to improve the heart valve function. These and other embodiments of the present invention are discussed herein.

The figures herein follow a numbering convention in which the first digit or digits correspond to the drawing figure number and the remaining digits identify an element or component in the drawing. Similar elements or components between different figures may be identified by the use of similar digits. For example, 110 may reference element "10" in FIG. 1, and a similar element may be referenced as 210 in FIG. 2. As will be appreciated, elements shown in the various embodiments herein can be added, exchanged, and/or eliminated so as to provide a number of additional embodiments of the valve according to the present invention.

FIG. 1 illustrates a schematic cross-section of a heart 100. The heart 100 is divided into four chambers, which are referred to herein as a first chamber 102, a second chamber 104, a third chamber 106 and a fourth chamber 108. With respect to the anatomy of the heart, the first chamber 102 can represent the left atrium, the second chamber 104 can represent the left ventricle, the third chamber 106 can represent the right atrium, and the fourth chamber 108 can represent the right ventricle. Other representations for the chambers 102, 104, 106 and 108 are also possible.

Heart 100 further includes heart valves positioned at either an inlet or an outlet of the four chambers of the heart 100. These heart valves include a mitral valve 114, an aortic valve 116, pulmonary valve 118, and tricuspid valve 120. Generally, each heart valve includes valve leaflets. For example, the structure of the mitral valve 114, the one-way heart valve that divides the first chamber 102 (i.e., the left atrium) and the second chamber 104 (i.e., the left ventricle), includes two leaflets. These two leaflets are referred to as the anterior leaflet 122-1 and the posterior leaflet 122-2. The anterior and posterior leaflets 122-1 and 122-2 move between an open position in which antegrade blood flow moves from the first chamber 102 to the second chamber 104, to a closed position that prevents retrograde flow of the blood from the second chamber 104 to the first chamber 102.

The anterior and posterior leaflets 122-1 and 122-2 are attached to a variety of structures that help to maintain the function of the mitral valve 114. For example, the mitral valve 114 includes a fibrous tissue ring structure, referred to as the mitral annulus 124, which surrounds and supports the anterior and posterior leaflets 122-1 and 122-2. The mitral annulus 124 can be conceptually divided into an anterior mitral annulus 126-1 and a posterior mitral annulus 126-2. The anterior leaflet 122-1 and posterior leaflet 122-2 are supported by the mitral annulus 124 by their connection to the anterior mitral annulus 126-1 and the posterior mitral annulus 126-2, respectively.

The mitral valve 114 further includes fibrous tissue called chordae tendineae 110. The chordae tendineae 110 function to tether the leaflets 122-1 and 122-2 of the mitral valve 114 to the ventricular walls 115. In addition, the mitral valve 114 also includes papillary muscles 112 that extend from the ventricular walls 115 to couple to the chordae tendineae 110. When the ventricles contract, the papillary muscles 112 pull the chordae tendineae 110 which act as tethers, and control the closure or coaptation of the valve leaflets 122-1 and 122-2, preventing them from flapping too far backwards (prolapse).

When operating properly, the mitral valve 114 acts as a one-way valve. There are, however, numerous conditions that can cause the mitral valve 114 to not act as a one-way valve. For example, deficiency or degeneration of one or more of the mitral valve 114 structures may result in dysfunction of the mitral valve apparatus leading to mitral valve prolapse or regurgitation during a contraction of the heart. Mitral valve prolapse is a condition in which blood leaks in the wrong direction (regurgitation of the blood) because one or more of the valve leaflets 122-1 and/or 122-2 close improperly. Reasons for why the valve leaflets 122-1 and/or 122-2 close improperly can include, for example, changes in the size and shape of the valves leaflets 122-1 and/or 122-2 and/or the mitral annulus 124 (e.g., an increase in the circumference of the mitral annulus 124).

Figure 2:
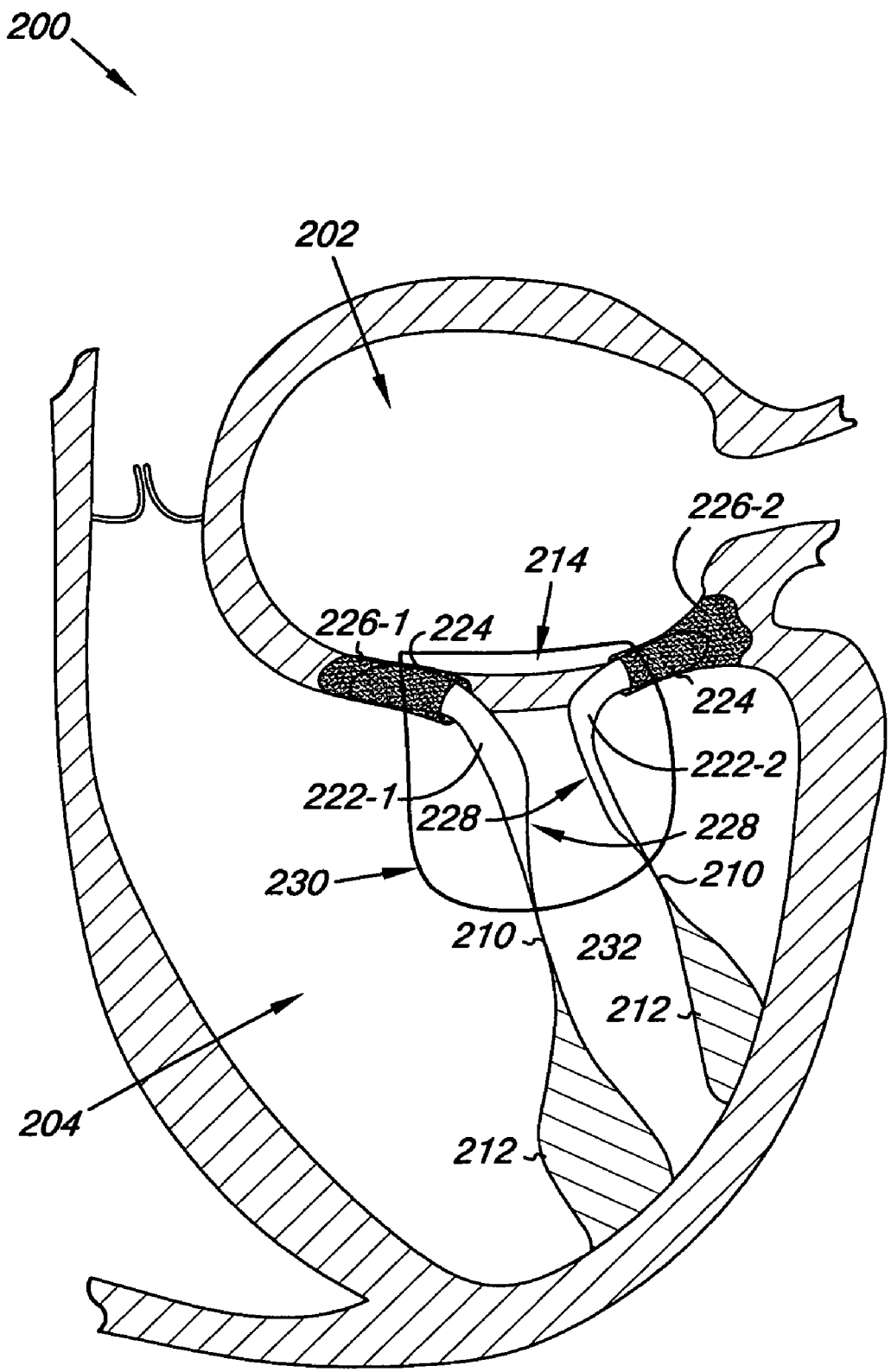
FIG. 2 provides a schematic cross-section of a heart, segments of which have been removed to show detail.

FIG. 2 illustrates a cross-section of the first chamber 202 and the second chamber 204 of the heart 200. In the present example, the valve leaflets 222-1 and 222-2 in their native state do not close properly, leading to the condition of mitral valve prolapse for the heart 200.

FIG. 2 also illustrates the presence of a cord 230 within the heart 200 according to various embodiments of the invention. The cord 230 can be delivered and positioned percutaneously within the heart 200, as discussed herein. The cord 230 allows for the configuration of the native heart valve to be modified in such a way that there can be an improvement in the functioning of the heart valve. In other words, the cord 230 can be used to change the physical relationship of the different parts of the heart valve in such a way as to help restore a more normal operation of the heart valve (e.g., reduce regurgitation of the blood).

In the illustration provided in FIG. 2, the heart valve being modified by the cord 230 is the mitral valve 214, as discussed herein. Other heart valves can be modified with the cord 230 so as to improve valve performance, where the number and relationship of one or more cords used to accomplish this goal depends upon the valve being modified. For example, a trileaflet heart valve, such as the aortic valve, might be modified using at least two cords having an approximately equilateral relationship (i.e., the at least two cords cross each other at a point to form an angle of approximately ninety (90) degrees). In an additional example, three cords could be used to modify the configuration of the valve, where the cords could have a predetermined relationship relative each other (i.e., the at least two cords cross each other at a point to form an angle of approximately sixty (60) degrees).

As will be discussed more fully herein, the cord 230 can be delivered to the heart valve (e.g., the mitral valve 214) by a delivery catheter. In one example, the delivery catheter can be used to pass a first end and a second end of the cord between the first heart chamber 202 and the second heart chamber 204, or visa versa. The first and second ends of the cord 230 can then be used in forming a loop around the heart valve. The length of the loop formed with the cord can then be manipulated (e.g., shortened) so as to modify the configuration of the heart valve.

In one embodiment, the configuration of the heart valve can be modified so as to induce coaptation of the valve leaflets at the proper time in the cardiac cycle. For example, the closed circumference of the loop formed with the cord 230 can have a constraining effect on the valve leaflets perpendicularly to the plane of their coaptation. The cord can also change the shape of the mitral annulus 224 in such a way that the valve leaflets 222-1 and 222-2 are drawn more closely together to allow for major surfaces 228 of the leaflets to seal when the valve 214 is in its closed configuration. In its open configuration, constraining the valve leaflets with the closed circumference of the loop formed with the cord 230 can further modify the heart valve to create a modified orifice (e.g., a double orifice) for the heart valve 214, where there had been an unmodified orifice (e.g., a single orifice) prior to the use of the cord 230.

As will be appreciated, a variety of apparatus and/or systems can be utilized in delivering and manipulating the cord 230. For example, delivery catheter based apparatus and/or systems can be utilized in delivering and manipulating the cord 230 according to a variety of the embodiments of the present invention. These apparatus and/or systems can both house the cord 230 and provide the structure through which the cord 230 can be delivered between the first heart chamber 202 and the second heart chamber 204. The following discussion provides various embodiments of the present invention.

Figure 3:
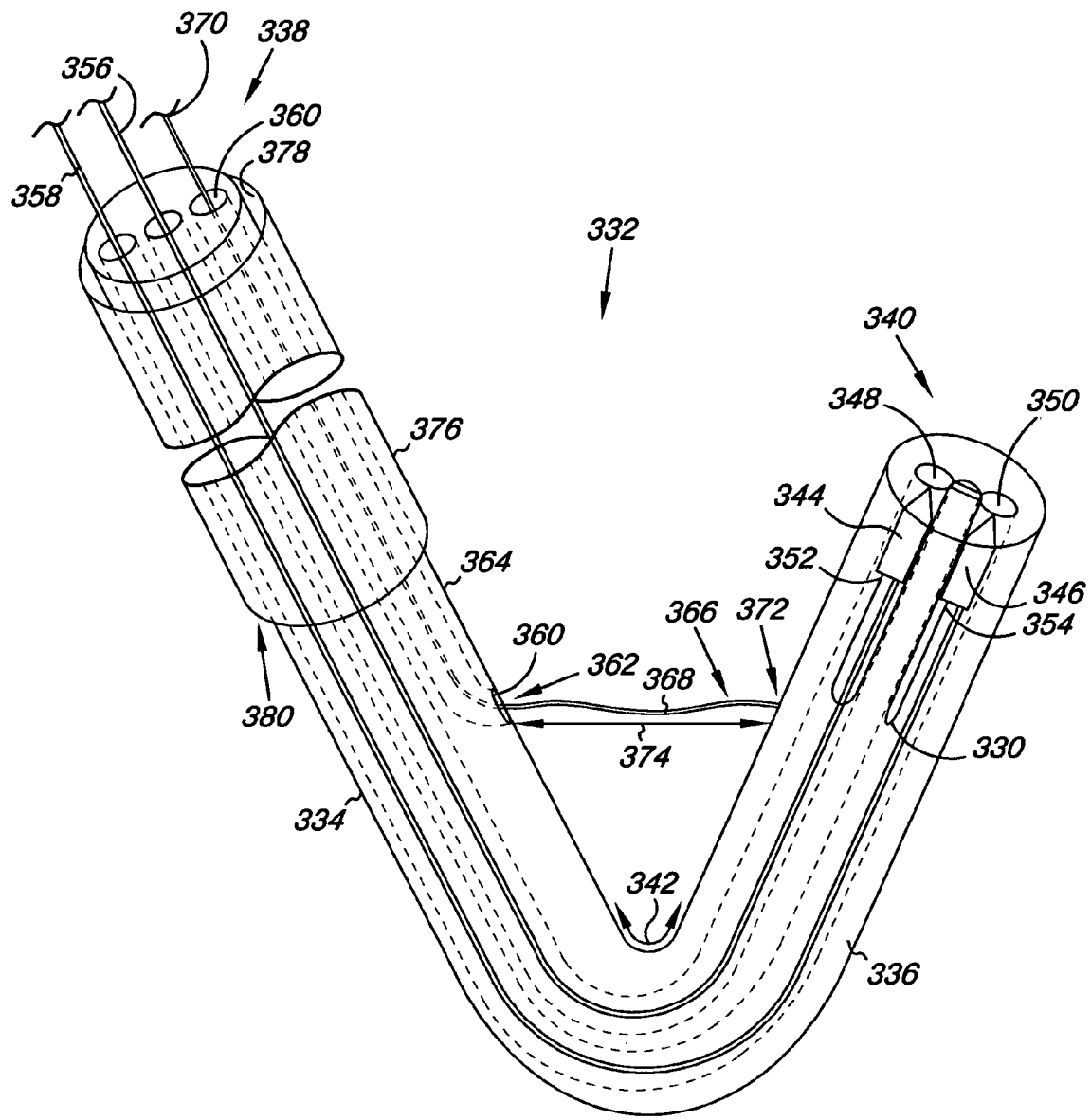
FIG. 3 illustrates one embodiment of an apparatus according to the present invention.

FIG. 3 provides a schematic illustration of an apparatus 332 according to one embodiment of the present invention. The apparatus 332 includes a delivery catheter 334 for positioning and passing at least a portion of the cord 330 between chambers of the heart, as discussed herein. The delivery catheter 334 has an elongate body 336 with a proximal end 338 and a distal end 340. The delivery catheter 334 further includes at least one predetermined bend 342 in the elongate body 336 between the proximal end 338 and the distal end 340. As discussed herein, the predetermined bend 342 allows the distal end 340 of the catheter 334 to be positioned adjacent the heart valve, such as the mitral valve, as will be discussed herein.

The delivery catheter 334 of the present embodiment further includes a first piercing member 344 and a second piercing member 346. The first and second piercing members 344 and 346 are releasably positioned at least partially within delivery catheter 334 in such a way that they can extend and separate from the delivery catheter 334. For example, as illustrated the first and second piercing members 344 and 346 are releasably positioned at least partially within a first lumen 348 and a second lumen 350, respectively, where the lumens 348 and 350 extend from the distal end 340 towards the proximal end 338 of the delivery catheter 334.

The first and second piercing members 344 and 346 can also be associated with the cord 330. For example, the first piercing member 344 can be associated with a first end 352 of the cord 330 and the second piercing member 346 can be associated with a second end 354 of the cord 330. In one embodiment, associating the cord 330 with the first and second piercing members 344 and 346 can include coupling the structures together. For example, the cord 330 can be severably coupled to the first piercing member 344 and the second piercing member 346. Such coupling can include, but is not limited to, chemically bonding the structures together (e.g., gluing), and/or physically bonding the structures together such as by melting/fusing the structures together and/or through frictional interactions such as results from, for example, a crimping process.

Alternatively, the first and second piercing members 344 and 346 could be formed from the cord 330 itself. For example, a portion of the cord 330 at or adjacent the first and second ends 352 and 354 of the cord 330 could be modified so as to form the first and second piercing members 344 and 346. Examples of such modifications include, but are not limited to, melting and/or fusing the cord 330 at and/or adjacent the first and second ends 352 and 354 to form at least a shaft having a sharp point to act as a piercing member.

FIG. 3 further illustrates that the cord 330 can be releasably positioned at least partially within the first and second lumen

348 and 350. In the present embodiment, the cord 330 can be released from the first and second lumen 348 and 350 as the first and second piercing members 344 and 346 are extended from the delivery catheter 334. In one embodiment, the cord 330 could at least partially reside in a groove that extends into the elongate body 336 from the first and second lumen 348 and 350. This allows the portion of the cord 330 adjacent the first and second piercing members 344 and 346 to avoid contacting each other as the piercing members are extended from the lumens 348 and 350. The groove can also function to hold the cord 330 and the first and second piercing members 344 and 346 in place in the lumens 348 and 350 through frictional interactions until the first and second piercing members 344 and 346 and the cord 330 are deployed.

The delivery catheter 334 further includes a first deployment rod 356 and a second deployment rod 358. In one embodiment, the first deployment rod 356 extends from the proximal end 338 through the first lumen 348 to abut the first piercing member 344. Similarly, the second deployment rod 358 extends from the proximal end 338 through the second lumen 350 to abut the second piercing member 346.

Both the first and second deployment rods 356 and 358 can be moved longitudinally within their respective lumens. In addition, the first and second deployment rods 356 and 358 provide a column strength, or a "pushability," to transfer force applied at their proximal end through to their distal end sufficient to extend the piercing members and cord from the delivery catheter 334 and into the cardiac tissue as discussed herein. As will be appreciated, the column strength of the deployment rods 356 and 358 will also be dependent upon the flexibility and strength of the lumen 348 and 350 in which the rod travels.

The first and second deployment rods 356 and 358, and the cord 330 can be formed from a number of different materials in a number of different configurations. For example, the rods 356 and 358 and/or the cord 330 can be formed of, by way of illustration and not by limitation, metals and/or metal alloys. For example, suitable metals and/or metal alloys include, but are not limited to, medical grade stainless steels (304, 306, 308, 316L, 318, etc.), gold, platinum, platinum alloys, palladium, rhodium, tungsten, tungsten alloys, cobalt chrome, titanium and titanium alloys, and other metal alloys such as those composed of titanium/nickel and sold under the trade identifier "nitinol." Other materials, such as polymer materials, may also be used.

Heat treatment of the nitinol alloy may also be desirable. An example of such a heat treatment includes, but is not limited to, placing the nitinol in its desired shape onto a mandrel. The nitinol is then heated to a temperature of 650°-750° F. for a predetermined time (e.g., two (2) to five (5) minutes), possibly (but not necessarily) annealing the constituent nitinol. After heat treatment, the flexible cord 330 retains its shape and the nitinol alloy retains its super-elastic properties.

By way of example, the cord 330 can be formed of a number of polymeric materials. For example, the cord 330 can be formed of, by way of illustration and not by limitation, thermoplastic and thermo-set polymers. Examples of these polymers include polyolefins such as polyethylene and polypropylene, polyesters such as Dacron, polyethylene terephthalate and polybutylene terephthalate, vinyl halide polymers such as polyvinyl chloride (PVC), polyvinylacetate such as ethyl vinyl acetate (EVA), polyurethanes, polymethylmethacrylate, pellethane, polyamides such as nylon 4, nylon 6, nylon 66, nylon 610, nylon 11, nylon 12 and polycaprolactam, polyaramids (e.g., KEVLAR), polystyrene-polyisobutylene-polystyrene (SIBS), segmented poly(carbonate-urethane), Rayon, fluoropolymers such as polytetrafluoroethylene (PTFE or TFE) or expanded polytetrafluoroethylene (ePTFE), ethylene-chlorofluoroethylene (ECTFE), fluorinated ethylene propylene (FEP), polychlorotrifluoroethylene (PCTFE), polyvinylfluoride (PVF), or polyvinylidenefluoride (PVDF), natural biopolymers such as cellulose, chitin, keratin, silk, and collagen, explanted veins, decellularized basement membrane materials, such as small intestine submucosa (SIS) or umbilical vein, or other naturally occurring extracellular matrix (ECM), and mixtures and copolymers thereof. SIS and ECM materials can be autologous, allogeneic or xenograft material derived from mammals, including sources, such as human, cattle, sheep, and porcine.

Each of the polymers noted herein may be used in conjunction with radiopaque filler materials such as barium sulfate, bismuth trioxide, bismuth carbonate, powdered tungsten, powdered tantalum, or the like so that the location of the cord 330 may be radiographically visualized within the human body.

In another embodiment of the present invention, the polymers and blends that are used to form the composite can be used as a drug delivery matrix. To form this matrix, the polymer would be mixed with a therapeutic agent. The variety of different therapeutic agents that can be used in conjunction with the polymers of the present invention is vast. In general, therapeutic agents which may be administered via the pharmaceutical compositions of the invention include, without limitation: antiinfectives such as antibiotics and antiviral agents; analgesics and analgesic combinations; anti-inflammatory agents; hormones such as steroids; and naturally derived or genetically engineered proteins, polysaccharides, glycoproteins, or lipoproteins. Matrix formulations may be formulated by mixing one or more therapeutic agents with the polymer. The therapeutic agent may be present as a liquid, a finely divided solid, or any other appropriate physical form. Typically, but optionally, the matrix will include one or more additives, such as diluents, carriers, excipients, stabilizers or the like. Additionally, radiopaque markers may be added to the composite to allow imaging of the composite after implantation.

The deployment rods 356 and 358, and/or the cord 330 can also include a variety of cross-sectional configurations. For example, the deployment rods 356 and 358, and/or the cord 330 can have one or more of a round (e.g., circular, oval, and/or elliptical), ribbon, semi-circular triangular, tubular, I-shaped, T-shaped, and trapezoidal. With respect to "braid," the term can include tubular constructions in which the cord 330 making up the construction are woven radially in an in-and-out fashion as they cross to form a tubular member defining a single lumen. The braid can also be constructed of flexible members of different widths. The embodiments, however, are not limited to the examples as other cross-sectional geometries are also possible.

In an additional embodiment, the cord 330 can include a number of forms that contribute to both its mechanical and handling properties. Examples of such forms for the cord 330 include, but are not limited to, those selected from the group consisting of weaves, braids, meshes, knits, warped knitted (i.e., lace-like), and non-woven structures, as the same will be known and understood by one of ordinary skill in the art. In addition, mechanical properties of the cord 330 can be altered by changing the density, form, and/or texture in one or more locations along the length of the cord 330. Examples of such changes include alterations to the suitable structures used to create the cord 330 which can include, for example, monofilaments, yarns, threads, braids, or bundles of fibers. Regardless of its configuration, the structure of the cord 330 should possess a tensile strength adequate to withstand pressures (e.g., a stretching load) imposed by manipulating the cord 330, as discussed herein.

The first and second piercing members 344 and 346 can also be formed from a number of different materials in a number of different configurations. For example, the first and second piercing members 344 and 346 can be formed of, by way of illustration and not by limitation, the materials discussed herein in conjunction with the cord 330. The first and second piercing members 344 and 346 can also include a variety of configurations. For example, the piercing members 344 and 346 can have one or more of a round (e.g., circular, oval, and/or elliptical), ribbon, semi-circular triangular, I-shaped, T-shaped, and trapezoidal cross-sectional configuration. The embodiments, however, are not limited to the present examples as other cross-sectional geometries are also possible. In addition, the piercing members 344 and 346 further include a leading edge or surface configured (e.g., sharp) to penetrate and pass through cardiac tissue under force applied by the respective deployment rod. In one embodiment, the leading edge can have a conical configuration ending in a point. Alternatively, the leading edge of the piercing member can be defined by one or more surfaces of the piercing members that have an edge having an angle (e.g., a 20 degree angle) to allow for the piercing members 344 and 346 to pass through the cardiac tissue.

The position of the distal end 340 can also be adjusted in a variety of ways. For example, the elongate body 336 can have a variety of shapes and curves that would be selected for appropriate use given the anatomy at hand. In this example, the elongate body 336 could have one or more predetermined bends or curves to meet demands for the placement of the catheter 334.

An additional embodiment could use a single curve design that can be modified by the operator during use of the catheter 334. For example, the delivery catheter 334 can further include a third lumen 360 extending from the proximal end 338 toward the distal end 340 of the delivery catheter 334. In one embodiment, the third lumen 360 has a surface defining an opening 362 through a wall 364 of the delivery catheter 334. The opening 362 can be positioned between the predetermined bend 342 and the proximal end 338 of the delivery catheter 334.

The delivery catheter 334 can further include an adjustment member 366 extending from the third lumen 360. As illustrated in FIG. 3, the adjustment member 366 has an elongate body 368 having a first end 370 and a second end 372. In one embodiment, the adjustment member 366 extends through the third lumen 360 with the first end 370 extending from the delivery catheter 334 at or adjacent the proximal end 338 of the catheter 334. In an additional embodiment, the second end of the adjustment member 366 can be coupled to the delivery catheter 334 at a point between the predetermined bend 342 and the distal end 340 of the catheter 334.

Applying tension (e.g., pulling and/or pushing) the adjustment member 366 from the first end 370 allows the second end 372 to move, thereby changing the predetermined bend 342. In other words, the predetermined bend 342 can flex under tension applied through the adjustment member to allow the distal end 340 to be positioned at a second predetermined location (discussed herein) adjacent the heart valve. When the tension on the adjustment member 366 is released, the predetermined bend 342 returns towards its original configuration prior to being changed by the adjustment member 366.

The second end 372 of the adjustment member 366 can be anchored into the elongate body 336 of the delivery catheter 334 in a number of ways. For example, the second end 372 of the adjustment member 366 can be mechanically anchored into the elongate body 336 of the catheter 334 with one or more barbs that resist/prevent the second end 372 of the adjustment member 366 from slipping or moving. Alternatively, the second end 372 of the adjustment member 366 can be secured to a cleat embedded in the elongate body 336 of the catheter 334. In an additional embodiment, the second end 372 of the adjustment member 366 can be chemically fastened (e.g., glued) to the elongate body 336 of the catheter 334. Combinations of these fastening methods, along with other fastening methods, are also possible.

The adjustment member 366 can be moved longitudinally within the third lumen 360 to change the position of the distal end 340 of the delivery catheter 334. For example, the adjustment member 366 can be pulled to provide tension at the second end 372 thereby reducing a distance 374 between the second end 372 and the opening 362 of the delivery catheter 334. The adjustment member 366 can also be used to push the elongate body 336 of the delivery catheter 334, thereby increasing the distance 374 between the second end 372 and the opening 362 of the delivery catheter 334. The pushing and/or pulling of the adjustment member 366 allows for temporary changes in the predetermined bend 342 and the relative position of the distal end 340 of the delivery catheter 334. In an additional embodiment, upon changing the predetermined bend 342 and the relative position of the distal end 340 of the delivery catheter 334 the adjustment member 366 can be temporarily locked to allow the position of the distal end 340 to be maintained.

The adjustment member 366 can also be formed from a number of different materials in a number of different configurations. For example, the adjustment member 366 can be formed of, by way of illustration and not by limitation, metals and/or metal alloys, as recited herein. Other materials, such as various polymer recited herein, may also be used. As will be appreciated, other structural configurations that allow for altering the shape and/or the position of the predetermined bend 342 and the relative position of the distal end 340 of the delivery catheter 334 are also possible. For example, a push-pull and/or torque wire(s) could be used with one or more lumens (e.g., the third lumen) that extend to the distal end 340 of the delivery catheter 334. The push or pull or push-pull wire(s) could then be use to provide a steerable catheter having a deflectable distal portion. As will be appreciated, a spring tube can also be provided at the distal portion of the delivery catheter 334 for improved torque transmission and kink-resistance. Example of suitable mechanisms for accomplishing delivery catheter steering can also be found in U.S. Pat. No. 5,318,525 to West et al., herein incorporated by reference in its entirety. Other examples are also possible.

The apparatus 332 can further include a sheath 376 having a lumen 378 large enough to receive and pass the delivery catheter 334. In one embodiment, the sheath 376 can be used to introduce the delivery catheter 334 into the heart, as will be discussed herein. Briefly, the sheath 376 can be introduced into and passed through the vasculature to position a distal end 380 of the sheath 376 into or adjacent a chamber of the heart. For example, the distal end 380 of the sheath 376 could be positioned across or adjacent the aortic valve. The delivery catheter 334 could then be extended from the sheath 376 to position the distal end 340 of the delivery catheter 334 at or adjacent the mitral valve of the heart from within the left ventricle of the heart. As will be appreciated, there are other locations that the distal end 380 of the sheath 376 could be positioned to allow access and positioning of the distal end 340 of the delivery catheter 334. In addition, it is appreciated that the sheath 376 can have one or more predetermined bends (i.e., a predetermined shape) that would allow for access and positioning of the distal end 340 of the delivery catheter 334 within the heart.

The sheath 376 can also be used to house the delivery catheter 334 upon its removal from the body. For example, the delivery catheter 334 can be retracted back into the lumen 378. In one embodiment, the distal end 380 of the sheath 376 is configured to assist in allowing the predetermined bend 342 in the elongate body 336 to straighten out as the delivery catheter 334 is retracted back into the lumen 378. For example, the distal end 380 of the sheath 376 can have a funnel like flare to allow the elongate body 336 not to "catch" on the distal end 380 of the sheath 376 as the predetermined bend 342 moves into the lumen 378.

In the various embodiments of the present invention, the elongate body of the delivery catheter 334 and the sheath 376 can be formed from a variety of materials and in a variety of configurations. For example, the materials may include, but are not limited to, polymer and polymer blends. Examples of such materials include, but are not limited to, polyurethane (PU), polyvinyl chloride (PVC), polyethylene (PE), polyolefin copolymer (POC), polyethylene terephthalate (PET), polyamid, mixtures, and block co-polymers thereof. As will be appreciated, selection of the material can be based generally on a broad range of technical properties, including, but not limited to, modulus of elasticity, flexural modulus, and Shore A hardness required for the embodiments of the present invention. Components of the present apparatus and/or system can also be coated for lubrication, for abrasion resistance, or to deliver one or more drugs and/or therapeutic agents.

In an additional embodiment, delivery catheter 334 can further include radiopaque markers. For example, radiopaque markers (e.g., attached, integrated, and/or coated), as discussed herein, can be used to mark the location of the first piercing member 344 and the second piercing member 346. In addition, radiopaque markers can be used to mark the location of cord 330. Other portions of delivery catheter 334 can also be marked with radiopaque markers as necessary to allow for visualization of the orientation and positioning of the delivery catheter 334.

Now referring to FIGS. 4A-4F, there is provided an illustration of an embodiment of an apparatus 482 according to the present invention. The apparatus 482 includes a receiving catheter 484 having an elongate body 486 with a proximal end 488 and a distal end 490. The receiving catheter 484 also includes a predetermined bend 492 positioned between the proximal and distal ends 488 and 490 of the elongate body 486. As discussed herein, the distal end 490 can be adjusted in a variety of ways. For example, the elongate body 486 can have a variety of shapes and curves that would be selected for appropriate use given the anatomy at hand. Alternatively, the position of the distal end 490 can be adjusted by the operator during use of the catheter 484, as discussed herein.

Figure 4A:
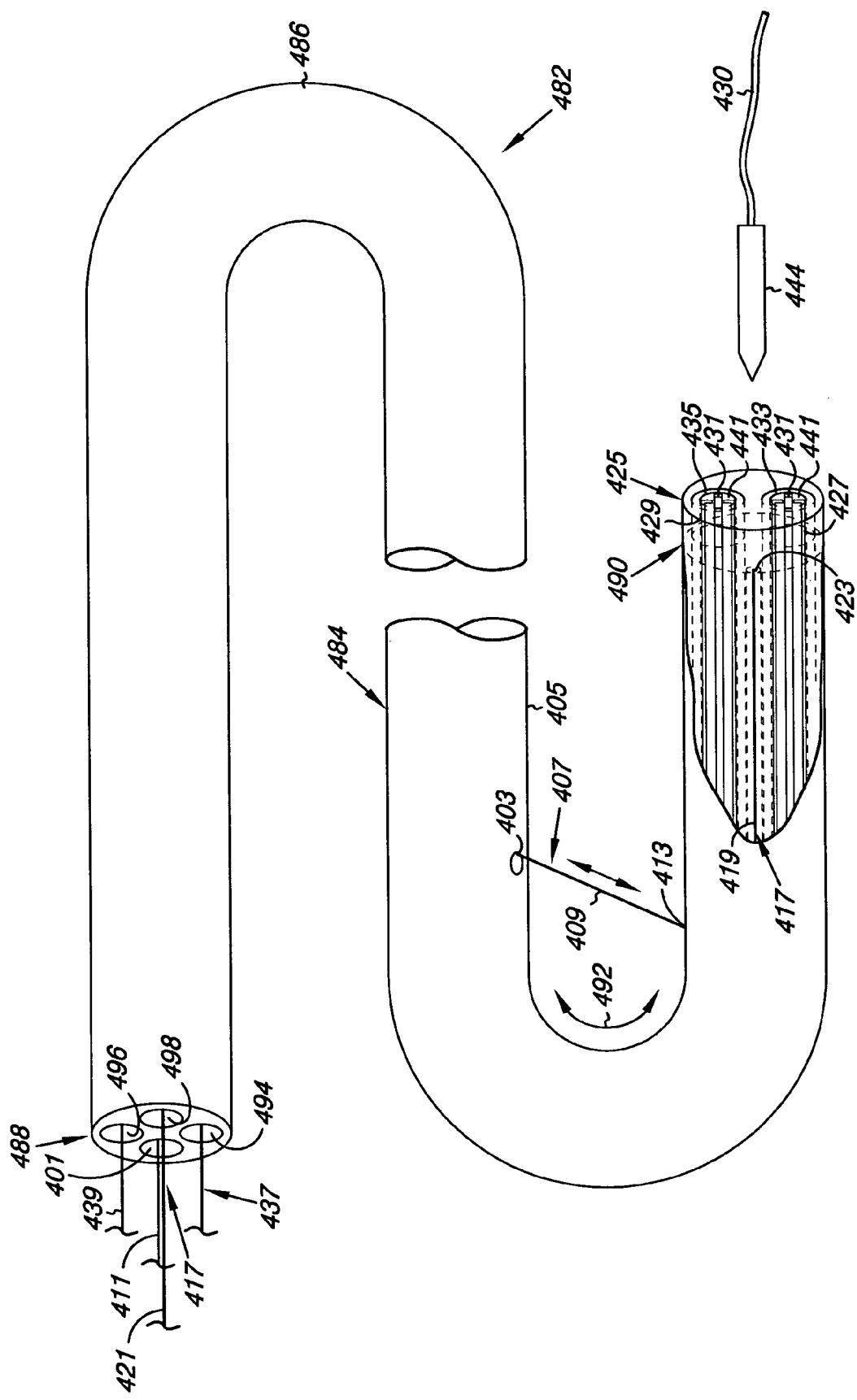
FIGS. 4A-4F illustrate one embodiment of an apparatus according to the present invention.
Figure 4B:
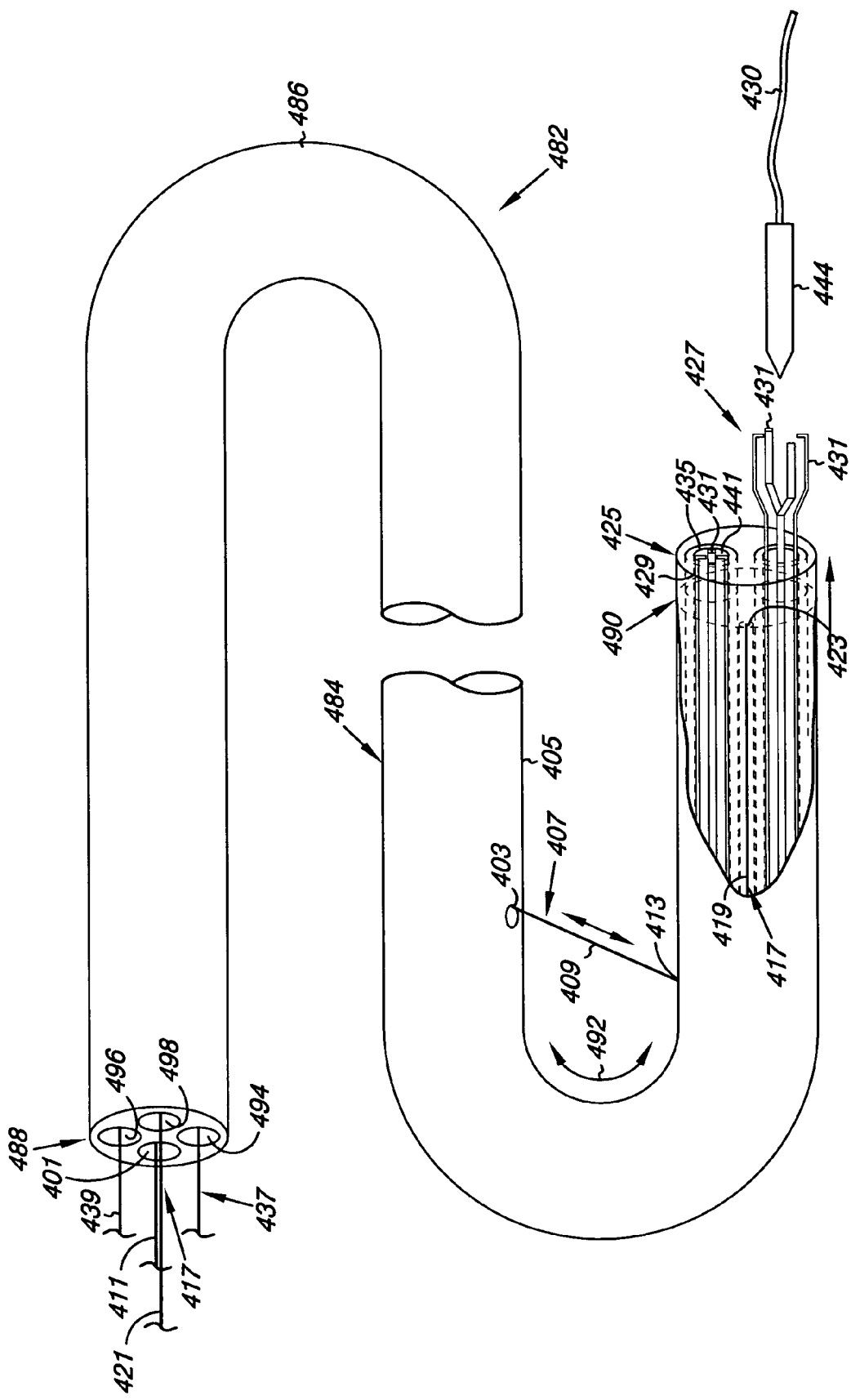
Figure 4C:
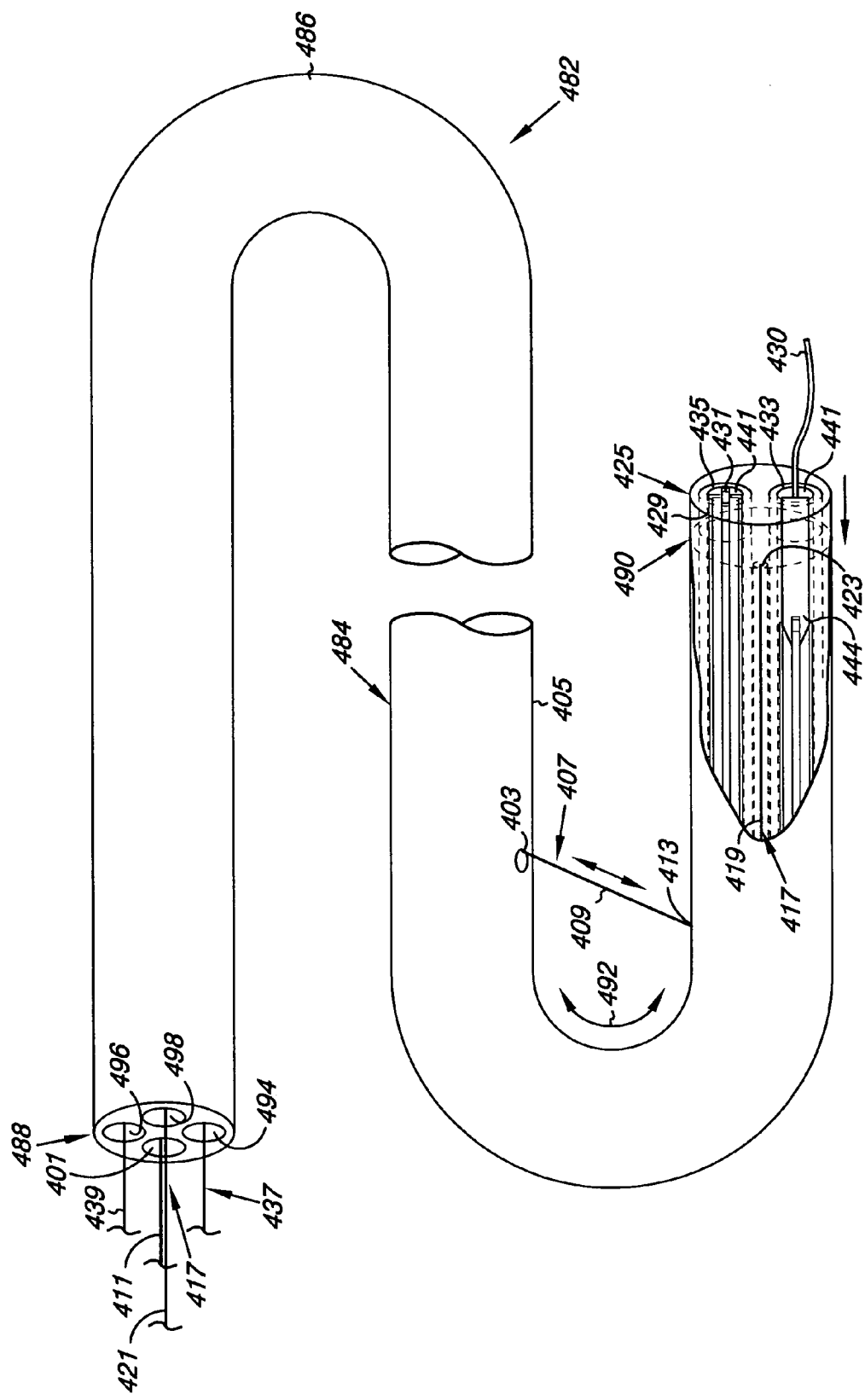
Figure 4D:
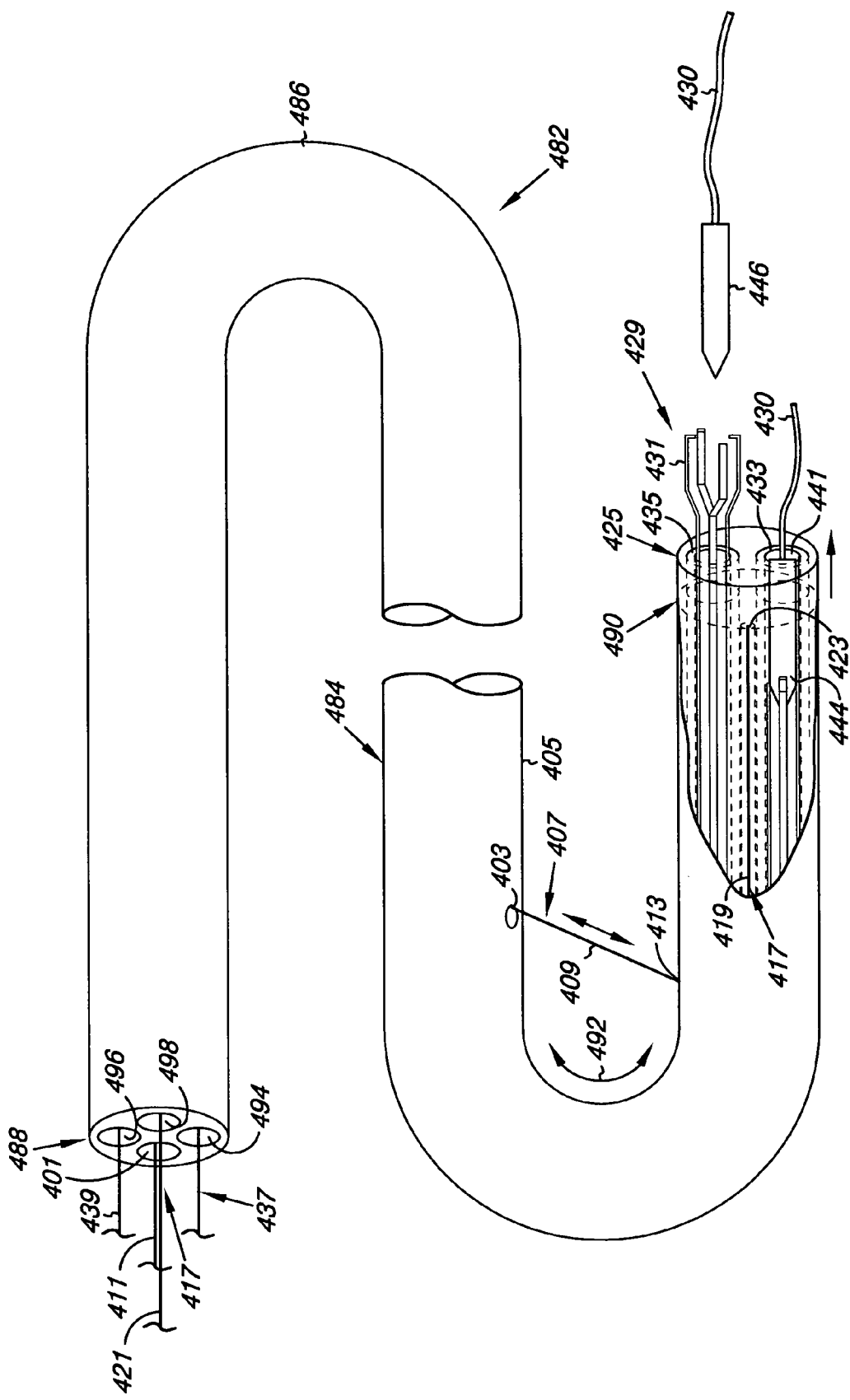

The receiving catheter 484 is adapted, as discussed herein, to interact with the cord 430, including the first and second piercing members 444, shown in FIG. 4A, and 446, shown in FIG. 4D. The receiving catheter 484 includes a first lumen 494, a second lumen 496, a third lumen 498, and a fourth lumen 401. In one embodiment, the first, second, and third lumens 494, 496, and 498 extend longitudinally within the elongate body 486 from the proximal end 488 to the distal end 490 of the receiving catheter 484. The fourth lumen 401 extends from the proximal end 488 toward the distal end 490 of the receiving catheter 484. In one embodiment, the fourth lumen 401 has a surface defining an opening 403 through a wall 405 of the receiving catheter 484. The opening 403 can be positioned between the predetermined bend 492 and the proximal end 488 of the receiving catheter 484.

The receiving catheter 484 also includes an adjustment member 407 extending from the fourth lumen 401. As illustrated in FIGS. 4A-4F, the adjustment member 407 has an elongate body 409 having a first end 411 and a second end 413. In one embodiment, the adjustment member 407 extends through the fourth lumen 401 with the first end 411 extending from the receiving catheter 484 at or adjacent the proximal end 488 of the catheter 484. In an additional embodiment, the second end of the adjustment member 407 can be coupled to the receiving catheter 484 at a point between the predetermined bend 492 and the distal end 490 of the catheter 484. In one embodiment, the adjustment member 407 can be anchored/coupled to the receiving catheter 484 as discussed above for adjustment member 366 illustrated in FIG. 3. In addition, the adjustment member 407 can be used to apply tension (e.g., pulling and/or pushing) from the first end 411 to allow the second end 413 to move, thereby changing the predetermined bend 492 in a similar manner as discussed above for adjustment member 366 illustrated in FIG. 3.

The adjustment member 407 can also be formed from a number of different materials in a number of different configurations. For example, the adjustment member 407 can be formed of, by way of illustration and not by limitation, metals and/or metal alloys, as recited herein. Other materials, such as various polymer recited herein, may also be used.

As will be appreciated, other structural configurations that allow for altering the shape and/or the position of the predetermined bend 492 and the relative position of the distal end 490 of the catheter 484 are also possible. For example, a push or pull or push-pull wire could be used with one or more lumen(s) (e.g., the fourth lumen) that extend to the distal end 490 of the catheter 484. As will be appreciated, other structural configurations that allow for altering the shape and/or the position of the predetermined bend 492 and the relative position of the distal end 490 of the receiving catheter 484 are also possible, such as those discussed herein in connection with FIG. 3.

The receiving catheter 484 further includes a release member 417 extending through the third lumen 498. The release member 417 includes an elongate body 419 having a first end 421 and a second end 423. In one embodiment, the release member 417 encircles the wall 405 of the elongate body 486 between the distal end 490 and a coupling device 425. As will be discussed herein, the coupling device 425 is used to join the cord 430 to form a loop. The coupling device 425 can then separate from the receiving catheter 484 through the use of the release member 417.

Figure 4E:
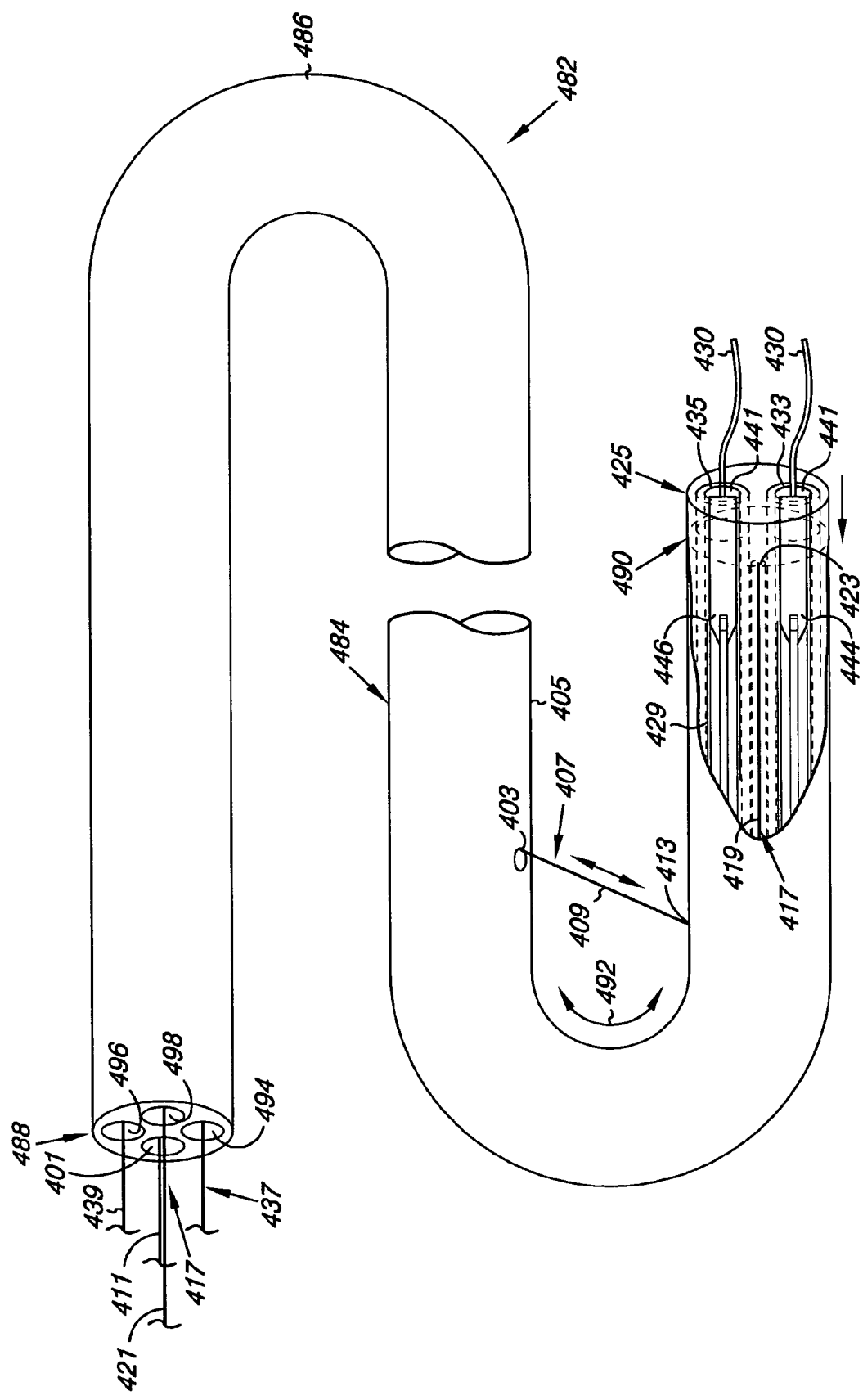
Figure 4F:
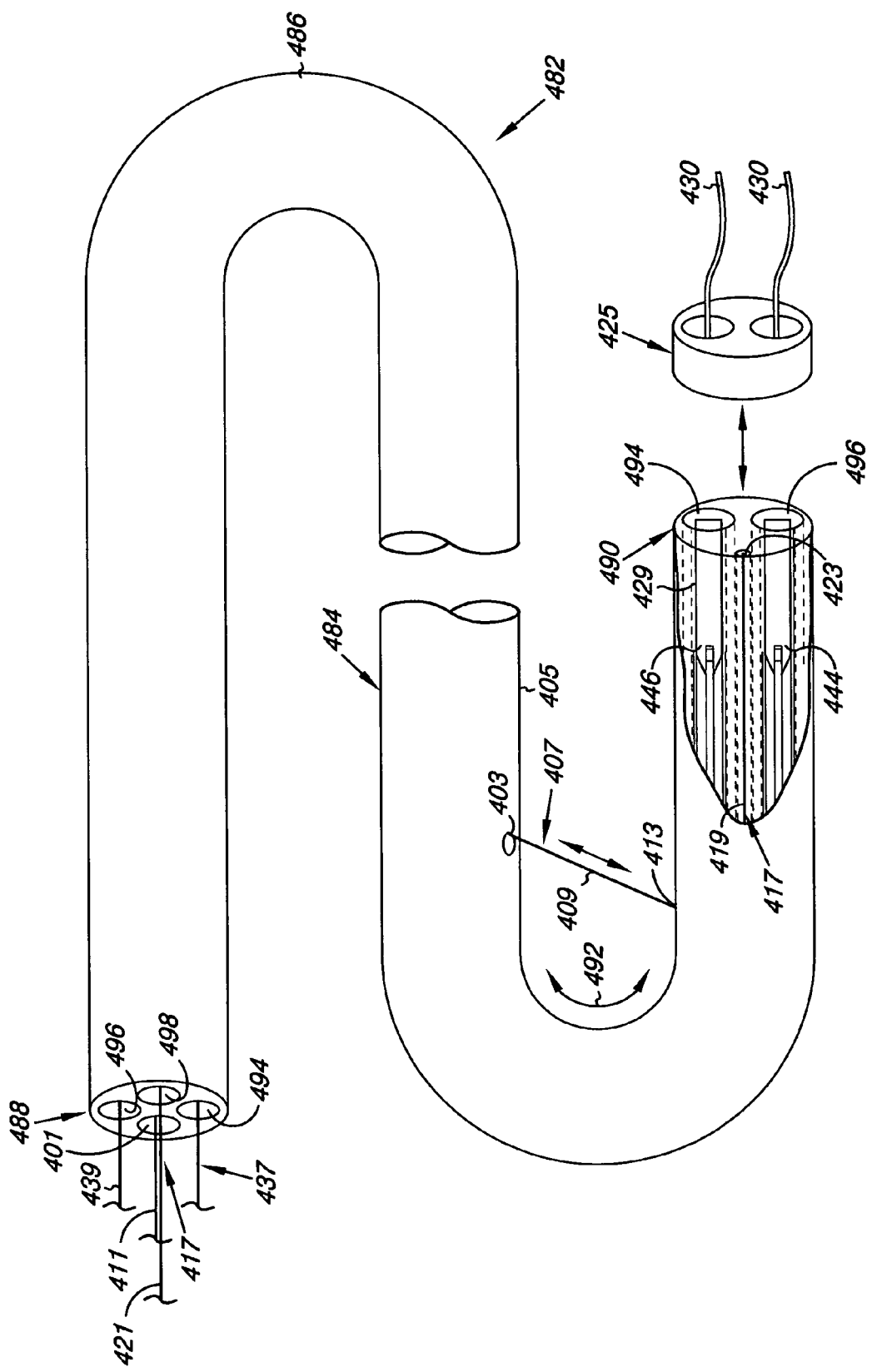

As illustrated in FIG. 4A, the release member 417 extends from the distal end 490 towards the wall 405 of the receiving catheter 484. In one embodiment, the release member 417 loops around the perimeter of the wall 405 perpendicularly to the elongate body 486. The release member 417 crosses itself where it emerges at the wall 405, returning towards the third lumen 498. In this way, the release member 417 completely encircles elongate body 486. The second end 423 of the release member 417 then couples to the elongate body 486 at or adjacent the third lumen 498 of the receiving catheter 484. The coupling device 425 can then be separated from the elongate body 486 of the receiving catheter 484 by applying sufficient tension (e.g., pulling) to the release member 417 so that it creates a cut between the through coupling device 425 and the elongate body 486 of the receiving catheter 484. FIG. 4F illustrates an embodiment in which the release member 417 has been used to separate the coupling device 425 and the elongate body 486 of the receiving catheter 484.

In one embodiment, to better ensure that the cut occurs between the coupling device 425 and the elongate body 486 of the receiving catheter 484, the distal end 490 of the elongate body 486 can be formed of a material that is harder (e.g., metal and/or polymer) than the material through which the release member 417 cuts. Similarly, the coupling device 425 can also be formed of a harder material than the material through which the release member 417 cuts. So, there can be a laminar structure in which both the distal end 490 of the elongate body 486 and the coupling device 425 are constructed of a first material and a second sacrificial material, softer than the first material, is used to connect the coupling device 425 to the elongate body 486. The release member 417 can then travel more easily through the second sacrificial material thereby better ensuring a clean separation of the elongate body 486 and the coupling device 425.

Other release mechanisms for separating the release member 417 and the coupling device 425 are also possible. For example, the second end 423 of the release member 417 can include a threaded portion that releasably engages a threaded socket in the coupling device 425. In this embodiment, the threaded engagement of the release member 417 holds the coupling device 425 to the receiving catheter 484 until torque is applied to the release member 417 to disengage the threaded connection with the coupling device 425. Once the threaded connection is disengaged, the coupling device 425 would be free of the receiving catheter 484. Other releasable coupling mechanisms are also possible, including the use of an electrolytic release mechanism.

The release member 417 can be constructed of a variety of materials and in a variety of configurations. For example, the release member 417 can be formed of, by way of illustration and not by limitation, metals and/or metal alloys, such as those discussed herein. Alternatively, the release member 417 can be formed from a number of polymeric materials, such as from many of those discussed herein. The deployment release member 417 can also include a variety of cross-sectional configurations. For example, the release member 417 can have one or more of a round (e.g., circular, oval, and/or elliptical), ribbon, semi-circular triangular, tubular, I-shaped, T-shaped, and trapezoidal. As will be appreciated, the release member 417 has a cross-sectional size that provides both sufficient strength and flexibility to perform its functions described herein.

The receiving catheter 484 further includes first retrieving members 427 and second retrieving members 429. Each of the first and second retrieving members 427 and 429 includes multiple fingers 431 that can be extended through first and second openings 433 and 435 of the coupling device 425. In one embodiment, as the fingers 431 extend from the first and second openings 433 and 435 then spread open to form a receiving area between the fingers 431 for the piercing member. For example, as illustrated in FIG. 4B the fingers 431 have been extended from the first opening 433. The fingers 431 have flared open to create the receiving area into which at least part of the piercing member 444 can be positioned. In one embodiment, the ends of the fingers 431 can be bent towards the center of the receiving area (e.g., hooked) to allow the fingers 431 to better engage the piercing member 444.

As illustrated, the fingers 431 can be extended from and retracted into the elongate body 486 of the receiving catheter 484 through the use of the fingers 431 that extend through the first and second lumen 494 and 496 of the elongate body 486. In one embodiment, the fingers 431 can be braided together to form a shaft 437 that extends through the proximal end 488 of the receiving catheter 484 to a predetermined location along the shaft 437. At the predetermined location, the fingers 431 transition from the braided structure into an aligned configuration in which the fingers 431 longitudinally extend in a radial fashion through the first and second lumens 494 and 496. Alternatively, the shaft 437 need not be formed from portions of the fingers 431. For example, the shaft 437 could be a member having one or more cross-sectional configurations described herein onto which the fingers 431 are coupled (e.g., welded). As illustrated, the fingers 431 have predetermined bends so the receiving area can be formed upon extending the fingers 431 from the receiving catheter 484.

Once captured, the shaft 437 can be pulled to draw the fingers 431, the first piercing member 444 and the cord 430 through the first opening 433 of the coupling device 425 and into the first lumen 494. This process is illustrated in FIGS. 4A-4C. The receiving catheter 484 can then be used to capture and retain the second piercing member 446 and the cord 430 in a similar manner. For example, FIGS. 4D and 4E illustrate the fingers 431 being extended from the second opening 433 in the coupling device 425 using the shaft 439. Once captured, the second piercing member 446 and the cord 430 can be drawn through the second opening 435 of the coupling device 425. The length of the cord 430 can then be adjusted (e.g., shortened) depending upon how far one or both of the first and/or second piercing members 444 and 446 and the cord 430 are drawn into the lumens 494 and 496 of the receiving catheter 484.

The fingers 431 and shafts 437 and 439 can also be formed from a number of different materials. For example, the fingers 431 and shafts 437 and 439 can be formed of, by way of illustration and not by limitation, metals and/or metal alloys, as recited herein. Other materials, such as various polymer recited herein, may also be used.

As discussed herein, the coupling device 425 includes the first opening 433 and the second opening 435. In one embodiment, the first opening 433 and the second opening 435 are defined by tabs 441. For example, each of the openings 433 and 435 can be defined by two or more tabs 441 that form a part of the coupling device 425. In one embodiment, as the fingers 431 having retrieved the piercing member 444 or 446 and cord 430 is drawn into the lumen 494 or 496, respectfully, the tabs 441 flex or bend to allow the structures to pass through the opening. Once the motion stops, however, the tabs 441 return to their un-flexed state to at least partially engage a structure located in the opening. For example, the openings 433 and 435 in their un-flexed state are able to physically engage the cord 430 thereby preventing the cord 430 from being drawn out of the opening once it has entered. In other words, the tabs 441 can function to form a one-way path for the cord 430 being drawn into either of the lumens 494 and 496.

In one embodiment, once the cord 430 has been draw into the openings 433 and 435, a loop is formed. The length of the loop formed by the cord 430 can then be adjusted by drawing the cord 430 though the "one-way" openings 433 and 435 of the coupling device. Once the length of the loop has been adjusted, the release member 417 can be used to separate the cord 430 in its looped configuration and the coupling device 425 from the elongate body 486 of the receiving catheter 484. In other words, the release member 417 is able to cut the cord 430 along with the material connecting the coupling device 425 and the elongate body 486 of the receiving catheter 484. An illustration of this can be seen in FIG. 4F.

The elongate body 486 of receiving catheter 484 can have various lengths between the proximal end 488 and the distal end 490. In one embodiment, the length between the proximal end 488 and the distal end 490 can be sufficient to allow the receiving catheter 484 to be percutaneously implanted through a patient's vasculature to position the distal end 490 at a predetermined location. Examples of the predetermined locations include, but are not limited to, cardiovascular locations such as on or adjacent to a cardiac valve of the heart (e.g., the mitral valve), including within a chamber of the patient's heart (e.g., the left atrium of the heart). As discussed above, the length between the proximal end 488 and the distal end 490 will be dependent upon each patient's physiological structure and the predetermined location within the patient.

Referring now to FIGS. 5A-5F, there is shown an embodiment of the apparatus 532 including both the sheath 576 and the delivery catheter 534. As discussed herein, the delivery catheter 534 can be used to position and deliver the cord 530. The cord 530 can then be formed into a loop, the length of which can be adjusted to modify the configuration of the heart valve in such as way as to induce coaptation of the valve leaflets.

In one embodiment, the cord 530 can be formed into a loop (illustrated in FIG. 2) having a closed circumference around a cardiac valve and positioned perpendicular to a plane of coaptation of the valve leaflets. The closed circumference of the loop can then be adjusted to provide a constraining effect on the valve leaflets perpendicularly to the plane of coaptation. Constraining the valve leaflets in this way can create a valve having a double orifice, which in turn, can help to reduce regurgitation through the cardiac valve, such as mitral valve regurgitation as discussed herein.

Figure 5A:
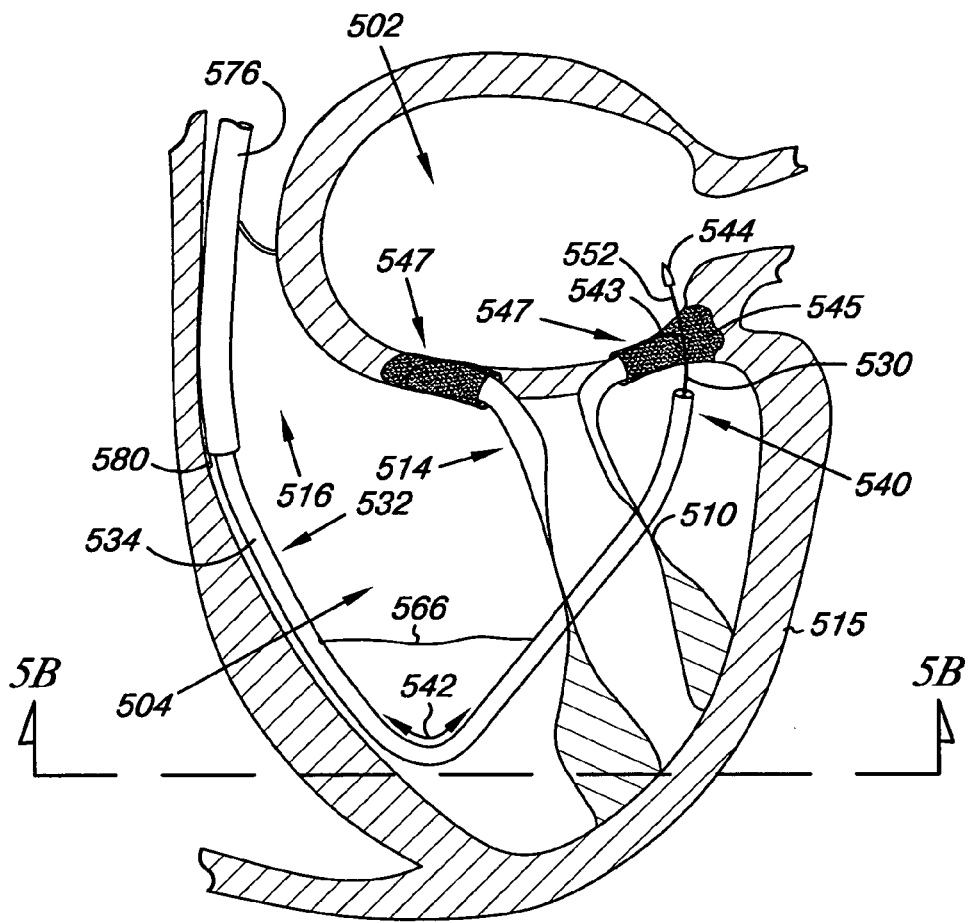
FIGS. 5A-5F illustrate one embodiment of an apparatus according to the present invention located within the cardiovascular system.

Referring now to FIG. 5A there is illustrated one embodiment of the apparatus 532 positioned within a cardiovascular system. In various embodiments, methods for modifying a cardiac valve can include positioning the delivery catheter 534 adjacent a heart valve. In one embodiment, positioning the delivery catheter 534 can include positioning the delivery catheter adjacent the fibrous ring surrounding the heart valve.

Specifically, the sheath 576 and the delivery catheter 534 are placed in such a way as to position the distal end 540 of the delivery catheter 534 at or adjacent a heart valve. In the present example, the heart valve is the mitral valve 514 located between the left atrium chamber (first chamber 502) and the left ventricle chamber (second chamber 504) of the heart 500. As will be appreciated, the delivery catheter 534 could be positioned at or adjacent another heart valve. Orientation and visualization of the various components and structures discussed herein may be accomplished through the use of any combination of echogenic, angioscopic, ultrasound and fluoroscopic visualization techniques.

Once in position, the delivery catheter 534 can then be used to pass the first end 552 of the cord 530 between the second heart chamber 504 (the left ventricle in this example) and the first heart chamber 502 (the left atrium in this example). To accomplish this, the sheath 576 can be introduced percutaneously into the arterial portion of the vasculature. In the present embodiment, the distal end 580 of the sheath 576 can be positioned across the aortic valve 516. The delivery catheter 534 can then be extended from the lumen 578 of the sheath 576, where upon emerging from the lumen 578 the predetermined bend 542 of the delivery catheter 534 can be reestablished.

The distal end 540 can then be positioned at a first predetermined location 543 by moving one or both the elongate body 536 of the delivery catheter 534 and the adjustment member 566, as discussed herein. In one embodiment, the distal end 540 of the delivery catheter 534 can be moved between the chordae tendineae 510 of the mitral valve 514 in positioning the distal end 540 of the delivery catheter 534 at or adjacent the first predetermined location 543 of the heart valve.

For example, the distal end 540 can be positioned at or adjacent a posterior portion 545 of a fibrous ring 547 surround the heart valve, such as the posterior mitral annulus of the mitral valve 514. Once in position, the first deployment rod can be used to extend the first piercing member 544 and the cord 530 from the delivery catheter 534. In one embodiment, the first piercing member 544 and a first portion of the cord 530 can be positioned within the fibrous ring 547 using the first deployment rod so at least the first piercing member 544 extends at least partially within the first heart chamber 502.

Figure 5B:
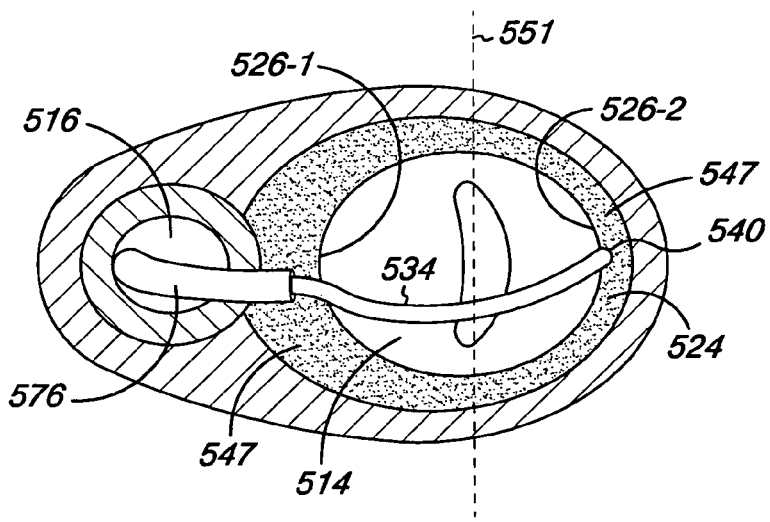

FIG. 5B illustrates a cross-sectional view of the mitral valve 514 taken along the line 5B-5B in FIG. 5A. FIG. 5B illustrates a view of the mitral valve 514 as seen from within from the left ventricle. As illustrated, the delivery catheter 534 extends from the aortic valve 516 to position the distal end 540 of the catheter 534 adjacent the fibrous ring 547 and the mitral annulus 524. This view of the catheter 534 also provides a further illustration of the implant location for the first piercing member 544 that allows the cord 530 to be positioned perpendicular to the plane of coaptation 551 of the mitral valve 514.

Figure 5C:
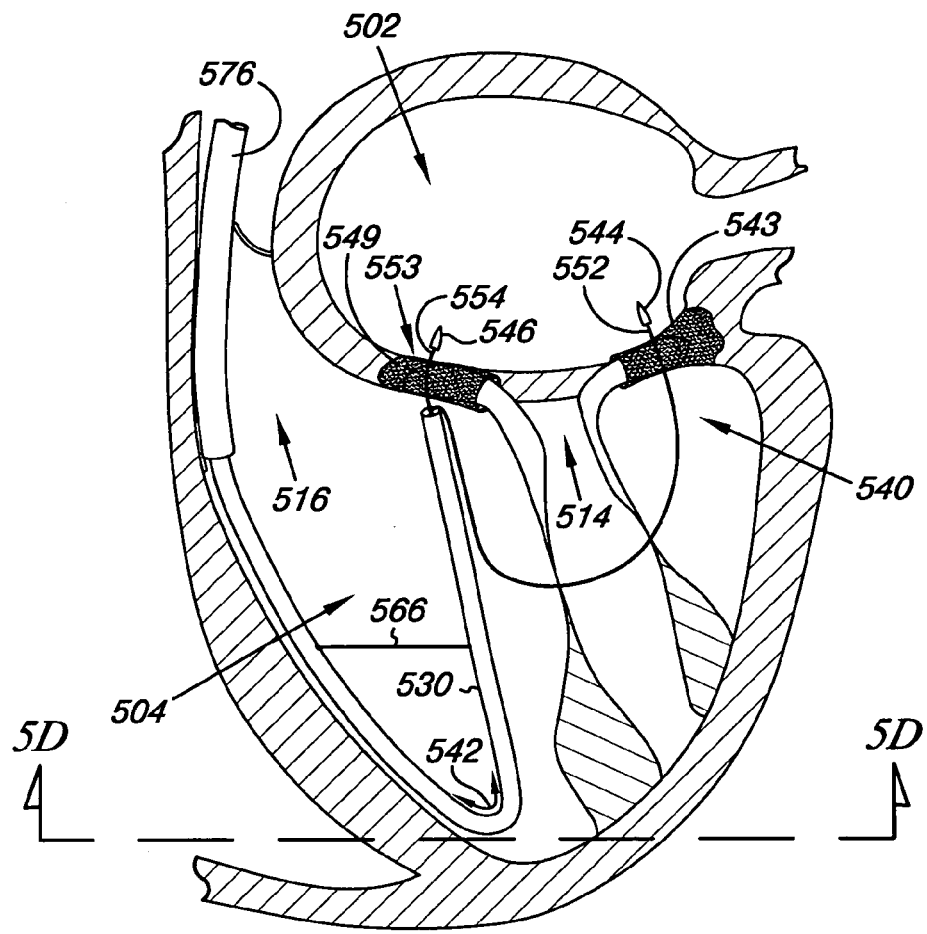

The distal end 540 can then be re-positioned, as illustrated in FIG. 5C, to a second predetermined location 553. In one embodiment, re-positioning to the second predetermined location 553 can be accomplished by moving one or both the elongate body 536 of the delivery catheter 534 and the adjustment member 566, as discussed herein. In the present example, the second predetermined location 553 can be an anterior portion 549 of the fibrous ring 547 surrounding the heart valve. In re-positioning, the cord 530 can also be positioned between at least a portion of the chordae tendineae 510 attached to leaflets of the heart valve with the delivery catheter 534. Once in position, the second piercing member 546 and a second portion of the cord 530 can be positioned within the fibrous ring 547 using the second deployment rod so at least the second piercing member 546 extends at least partially within the second heart chamber 504.

Figure 5D:
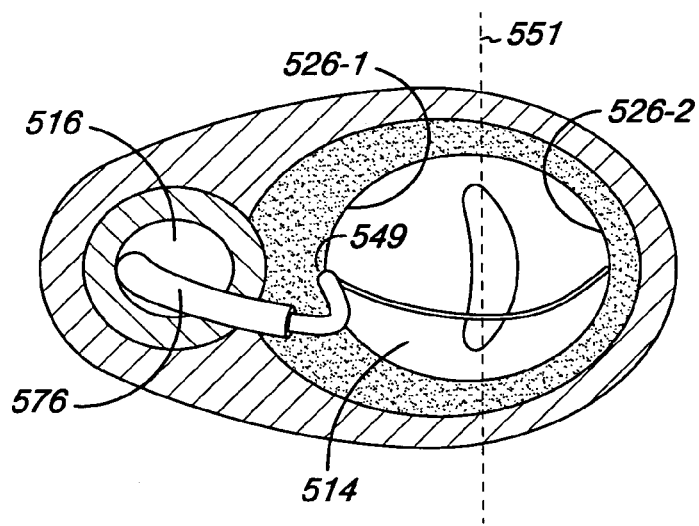

FIG. 5D illustrates a cross-sectional view of the mitral valve taken along the line 5D-5D in FIG. 5C. FIG. 5D illustrates a view of the mitral valve 514 as seen from within from the left ventricle. As illustrated, the delivery catheter 534 extends from the aortic valve 516 to position the distal end 540 of the catheter 534 adjacent the fibrous ring 545 and the mitral annulus 524. This view of the catheter 534 also provides a further illustration of the implant location for the second piercing member 546 that allows the cord 530 to be positioned perpendicular to the plane of coaptation 551 of the mitral valve 514.

Figure 5E:
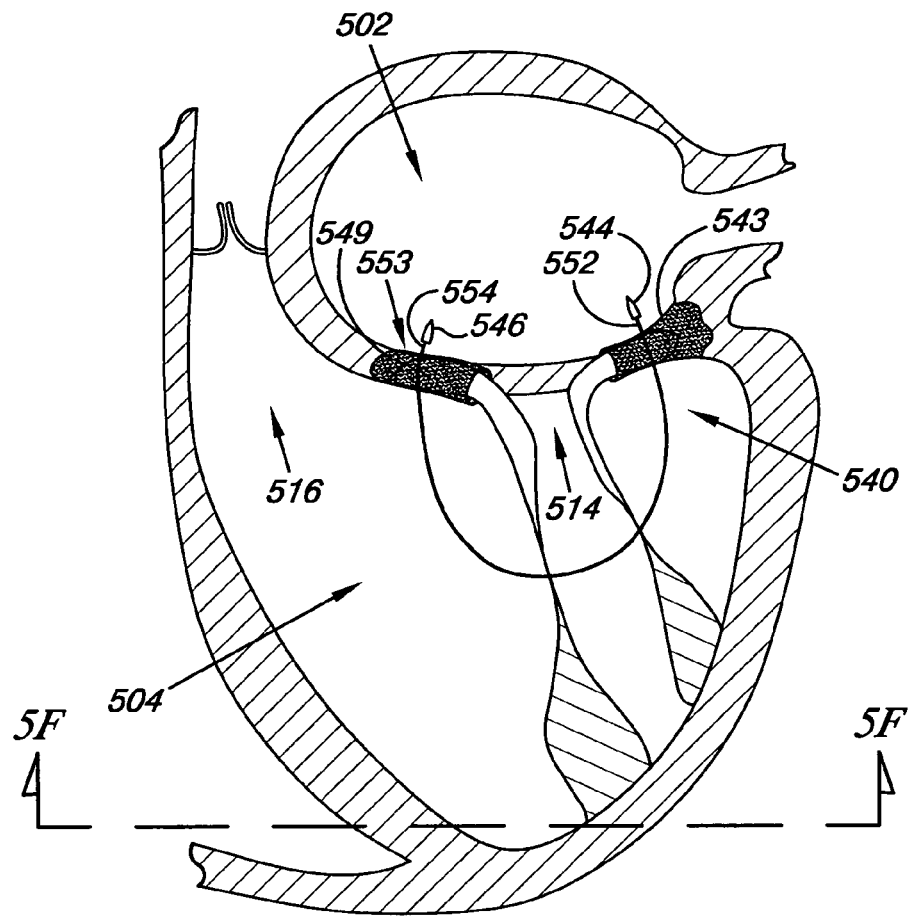
Figure 5F:
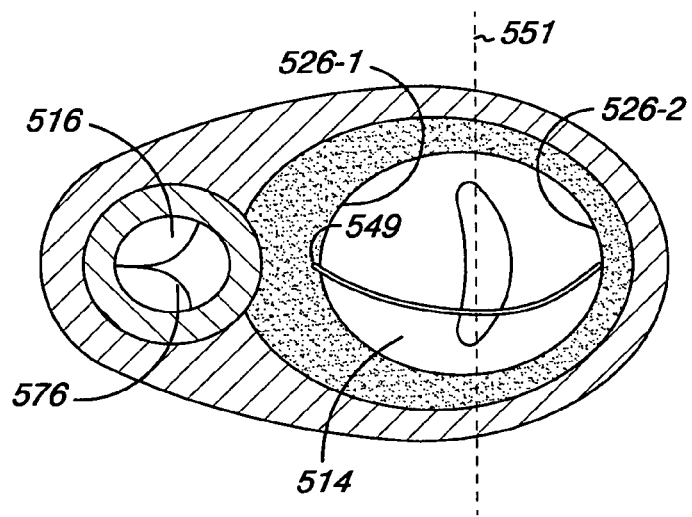

Once the second piercing member 546 and the second portion of the cord 530 are positioned within the fibrous ring 547, the delivery catheter 534 can be retracted back into the sheath 576, and the apparatus 532 removed from the vasculature. FIGS. 5E and 5F provide an illustration of this embodiment.

Referring now to FIGS. 6A-6F, there is shown an embodiment of the apparatus 682 including both a sheath 655 and the receiving catheter 684. As discussed herein, the receiving catheter 684 can be used to interact with the cord 630, including the first and second piercing members 644 and 646. The receiving catheter 684 can also be used in forming the cord 630 into a loop that can be separated from the receiving catheter 684. In addition to forming the loop, the receiving catheter 684 can also be used in adjusting the length of the cord 630 forming the loop to modify the configuration of the heart valve in such as way as to induce coaptation of the valve leaflets.

Figure 6A:
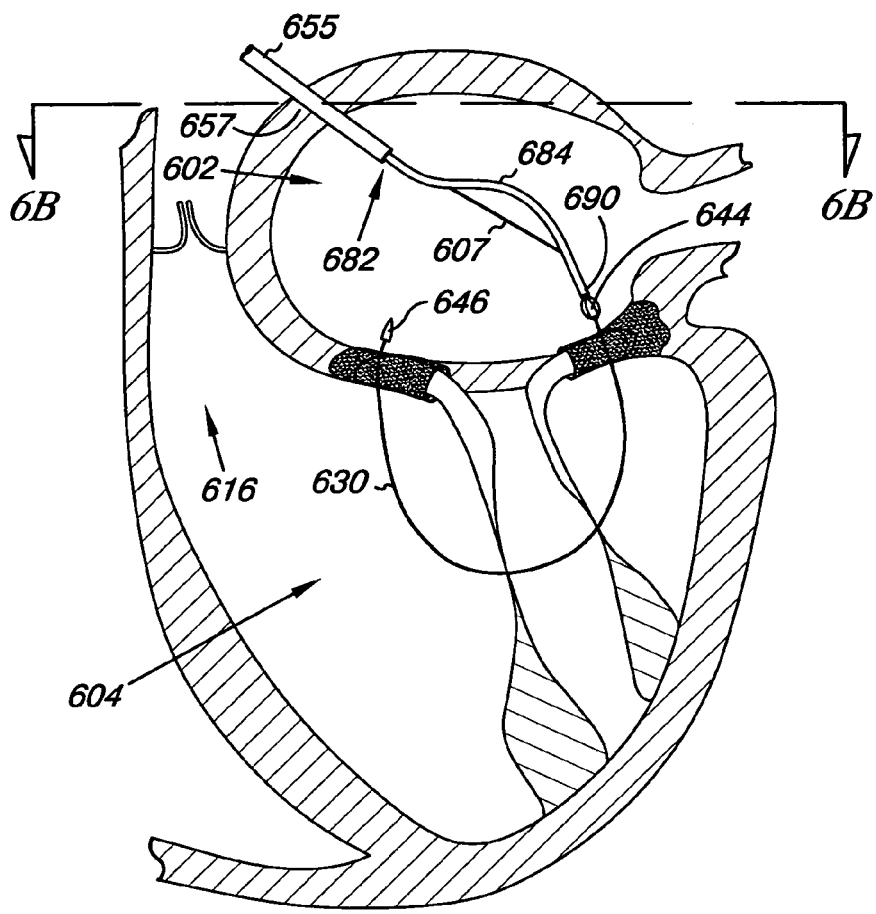
FIGS. 6A-6F illustrate one embodiment of an apparatus according to the present invention located within the cardiovascular system.

Referring now to FIG. 6A there is illustrated one embodiment of the apparatus 682 positioned within a cardiovascular system. In various embodiments, methods for modifying a cardiac valve can include positioning the receiving catheter 684 adjacent a heart valve. In one embodiment, positioning the receiving catheter 684 can include positioning the delivery catheter adjacent the fibrous ring surrounding the heart valve.

Specifically, the sheath 655 and the receiving catheter 684 are placed in such a way as to position the distal end 690 of the receiving catheter 684 at or adjacent a heart valve in the first heart chamber 602, such as the mitral valve 614. To accomplish this, the sheath 655 can be introduced percutaneously into the left atrium (the first heart chamber 602) by crossing the interatrial septum 657. The receiving catheter 684 can then be extended from the sheath 655 to position the distal end 690 adjacent the heart valve.

As will be appreciated, the receiving catheter 684 could be positioned at or adjacent another heart valve. Orientation and visualization of the various components and structures discussed herein may be accomplished through the use of any combination of echogenic, angioscopic, ultrasound and fluoroscopic visualization techniques.

The distal end 690 can then be positioned adjacent the first piercing member 644 and/or the cord 630 by either selecting the appropriate shaped elongate body and/or moving one or both the elongate body 686 of the receiving catheter 684 and the adjustment member 607, as discussed herein. Once in position, the receiving catheter 684 can then be used to capture the first piercing member 644 and/or at least a first portion of the cord 630. In one embodiment, the fingers of the receiving catheter 684 can be used to capture and draw the first piercing member 644 and/or at least a first portion of the cord 630 into the first opening of the coupling device, as discussed herein. FIG. 6A provides an illustration of the first piercing member 644 being captured and drawn into the receiving catheter 684.

Figure 6B:
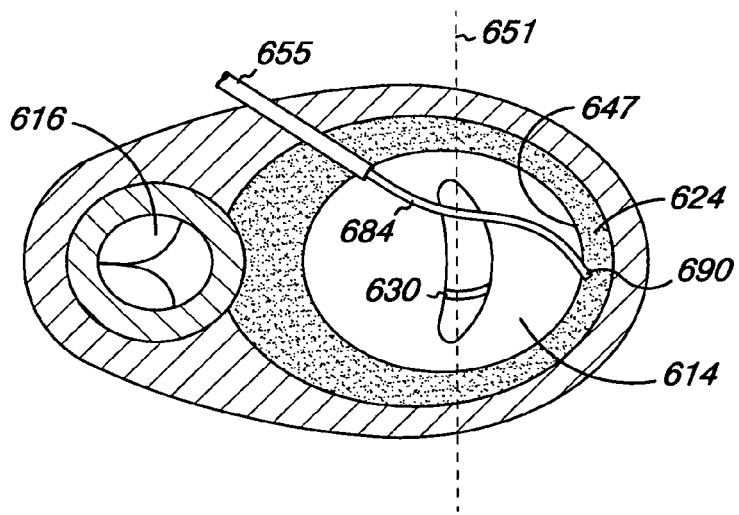

FIG. 6B illustrates a cross-sectional view of the mitral valve taken along the line 6B-6B in FIG. 6A. FIG. 6B illustrates a view of the mitral valve 614 as seen from within from the left atrium. As illustrated, the receiving catheter 684 extends from the sheath 655 to position the distal end 690 of the catheter 684 adjacent the fibrous ring 647 and the mitral annulus 624. This view of the catheter 684 also provides a further illustration of the implant location for the first piercing member 644 that allows the cord 630 to be positioned perpendicular to the plane of coaptation 651 of the mitral valve 614.

Figure 6C:
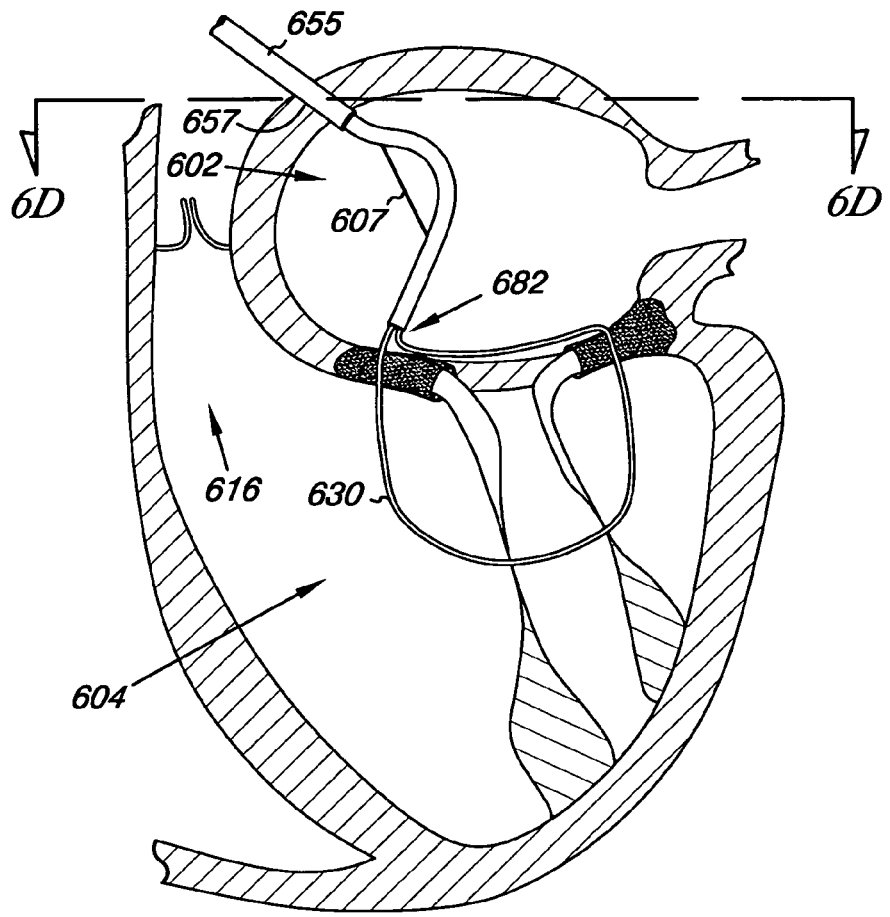

The distal end 690 can then be re-positioned, as illustrated in FIG. 6C, adjacent the second piercing member 646 and/or the cord 630 by moving one or both the elongate body 686 of the receiving catheter 684 and the adjustment member 607, as discussed herein. Once in position, the receiving catheter 684 can then be used to capture the second piercing member 646 and/or at least a second portion of the cord 630. In one embodiment, the fingers of the receiving catheter 684 can be used to capture and draw the second piercing member 646 and/or at least a second portion of the cord 630 into the second opening of the coupling device, as discussed herein. FIG. 6C provides an illustration of the second piercing member 646 being captured and drawn into the receiving catheter 684.

Figure 6D:
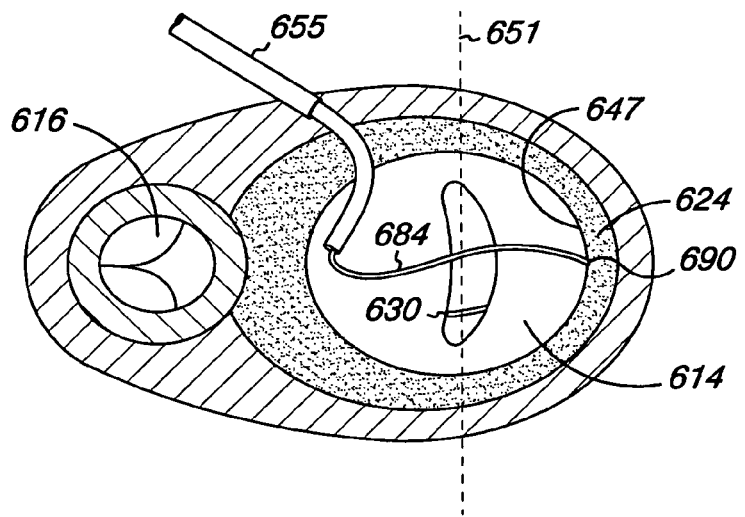
Figure 6E:
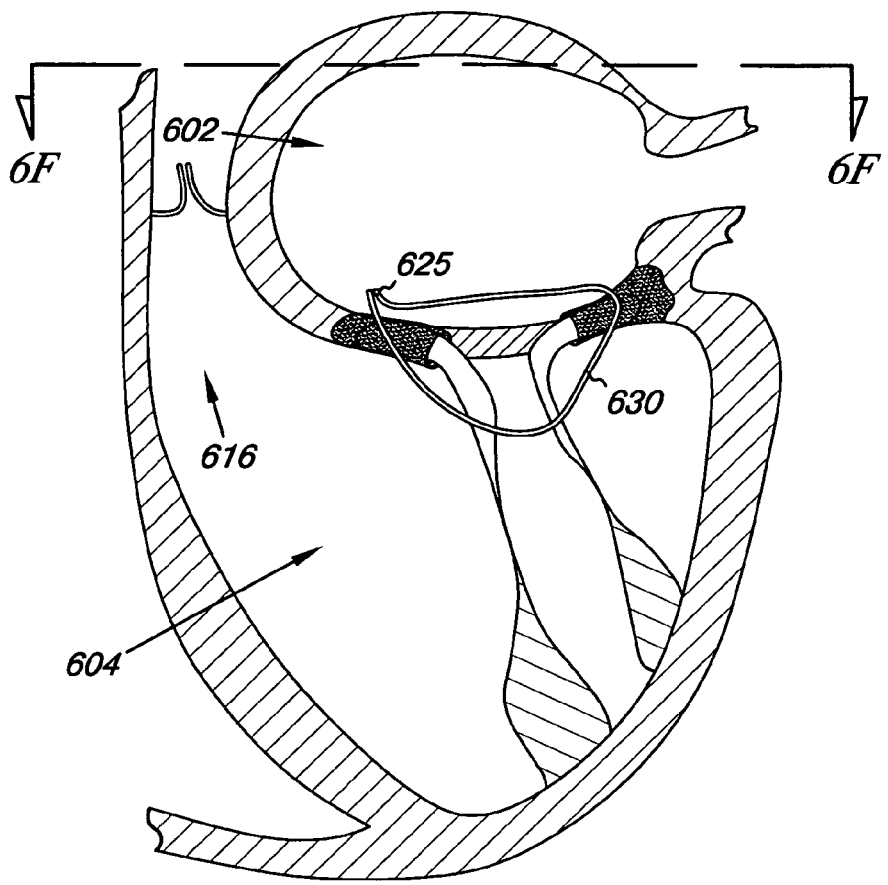
Figure 6F:
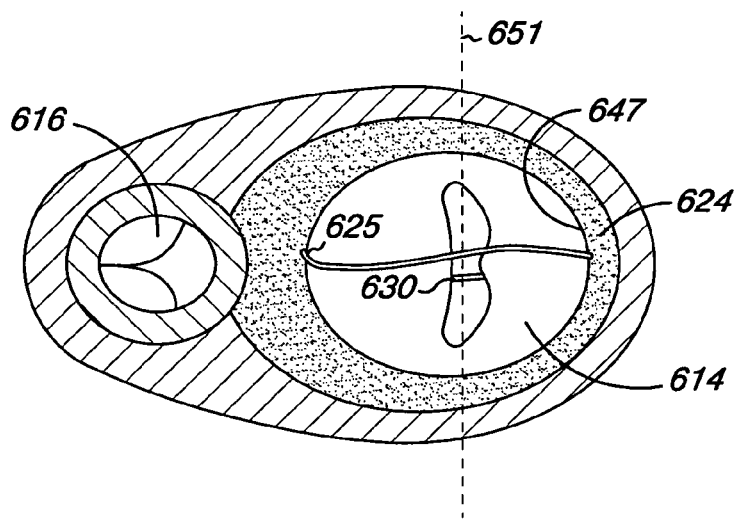

FIG. 6D illustrates a cross-sectional view of the mitral valve taken along the line 6D-6D in FIG. 6C. FIG. 6D illustrates a view of the mitral valve 614 as seen from within from the left atrium. As illustrated, the receiving catheter 684 has drawn the cord 630 perpendicularly across the plane of coaptation 651 of the mitral valve 614.

Once the second piercing member 646 and the second portion of the cord 630 are captured and drawn into the receiving catheter 684 a loop having a closed circumference is formed. The length of the looped cord 630 can then be manipulated (e.g., adjusting the length) so as to alter the configuration of the heart valve so as to induce the leaflets of the heart valve to coapt. In one embodiment, adjusting the length of the cord 630 can be used to adjust the tension of the cord 630 so as to apply force to the anterior and posterior portion of the fibrous ring of the heart valve.

Adjusting tension of the cord 630 through the receiving catheter 684, as discussed herein, can be used to modify the configuration of the heart valve. In one embodiment, altering the configuration of the heart valve includes constraining the elongate portion of the valve leaflets of the heart valve perpendicularly to the plane of coaptation so as to create a double orifice through an opening of the mitral valve 614. The cord 630 in its loop form, along with the coupling device, can then be released from the receiving catheter 684 through the use of the release member, as discussed herein.

The present invention further includes a medical system. In one embodiment, the medical system of the present invention includes both the apparatus 332, as illustrated in FIG. 3, and the apparatus 482, as illustrated in FIGS. 4A-4F.

While the present invention has been shown and described in detail above, it will be clear to the person skilled in the art that changes and modifications may be made without departing from the scope of the invention. As such, that which is set forth in the foregoing description and accompanying drawings is offered by way of illustration only and not as a limitation. The actual scope of the invention is intended to be defined by the following claims, along with the full range of equivalents to which such claims are entitled.

In addition, one of ordinary skill in the art will appreciate upon reading and understanding this disclosure that other variations for the invention described herein can be included within the scope of the present invention. For example, the delivery and receiving catheters can be coated with a non-thrombogenic biocompatible material, as are known or will be known.

In the foregoing Detailed Description, various features are grouped together in several embodiments for the purpose of streamlining the disclosure. This method of disclosure is not to be interpreted as reflecting an intention that the embodiments of the invention require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. An apparatus, comprising:
   a receiving catheter having a proximal end and a distal end, and a predetermined bend there between that positions the distal end adjacent a fibrous ring surrounding a heart valve;
   a first lumen and a second lumen extending from the distal end towards the proximal end of the receiving catheter;
   a first capture device positioned at least partially within the first lumen, wherein the first capture device extends from the receiving catheter and captures a first piercing member and a first portion of a cord protruding from the fibrous ring and houses the captured first piercing member and the first portion of the cord in the first lumen;
a second capture device positioned at least partially within the second lumen, wherein the second capture device extends from the receiving catheter and captures a second piercing member and a second portion of the cord protruding from the fibrous ring and houses the captured second piercing member and the second portion of the cord in the second lumen;
a coupling device directly connected to the distal end of the receiving catheter and having a first opening aligned with the first lumen and a second opening aligned with the second lumen such that the first capture device passes through the first opening and the second capture device passes through the second opening, wherein the coupling device connects to the first and second portions of the cord and forms a loop including the coupling device, and wherein the coupling device and loop are separable from the distal end of the receiving catheter, and wherein a portion of the coupling device proximal to the distal end of the receiving catheter is constructed of a sacrificial material, softer than a material used to construct a remainder of the coupling device; and
a release member associated with the receiving catheter and the coupling device, wherein the release member is configured to cut the cord extending beyond the loop and to cut through the sacrificial material to separate the coupling device and the loop from the receiving catheter.

2. A medical system, comprising:
a delivery catheter having:
  a first lumen and a second lumen extending from a distal end towards a proximal end of the delivery catheter;
  a first piercing member and a second piercing member, the first piercing member releasably positioned at least partially within the first lumen, and the second piercing member releasably positioned at least partially within the second lumen; and
  a cord directly coupled to the first piercing member and the second piercing member, and releasably positioned within the delivery catheter such that the first piercing member, the second piercing member and the cord egress from the distal end of the delivery catheter and separate and disengage from the distal end of delivery catheter, wherein a length of the cord in a non-strained state is:
    sufficient to form a loop around the heart valve; and
    greater than a length sufficient to constrain the heart valve in a configuration where the cord forms the loop around the heart valve; and
a receiving catheter having:
  a third lumen and a fourth lumen extending from a distal end towards a proximal end of the receiving catheter;
  a capture device positioned at least partially within at least one of the third or fourth lumens, wherein the capture device extends from the receiving catheter and captures a portion of the first piercing member and the second piercing member and houses the captured portion of the first piercing member in the third lumen and the second piercing member in the fourth lumen; and
  a coupling device connected to the distal end of the receiving catheter and having an opening aligned with at least one of the third and fourth lumens such that the capture device passes through the opening, wherein the coupling device connects a first and second portion of the cord and forms the loop including the coupling device, and wherein the coupling device and the loop separate from the distal end of the receiving catheter.

3. The system of claim 2, further including a first deployment member extending through the first lumen of the delivery catheter to contact the first piercing member.

4. The system of claim 3, further including a second deployment member extending through the second lumen of the delivery catheter to contact the second piercing member, wherein the first and second deployment members can move to extend the first and second piercing members from the first and second lumen of the delivery catheter.

5. The system of claim 2, further including a fifth lumen extending from the proximal end toward the distal end of the delivery catheter, the fifth lumen having a surface defining an opening through a wall of the delivery catheter between the predetermined bend and the proximal end of the delivery catheter.

6. The system of claim 5, further including an adjustment member extending from the fifth lumen and coupled to the delivery catheter at a point between a predetermined bend in the delivery catheter and the distal end of the delivery catheter.

7. The system of claim 6, wherein the predetermined bend flexes under tension applied through the adjustment member.

* * * * *